United States Patent
Millman et al.

(10) Patent No.: US 10,597,639 B2
(45) Date of Patent: Mar. 24, 2020

(54) 3D-PRINTED SCAFFOLD DEVICE FOR CELL TRANSPLANTATION

(71) Applicants: Jeffrey Millman, St. Louis, MO (US); Jiwon Song, St. Louis, MO (US)

(72) Inventors: Jeffrey Millman, St. Louis, MO (US); Jiwon Song, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/788,989

(22) Filed: Oct. 20, 2017

(65) Prior Publication Data

US 2018/0119106 A1 May 3, 2018

Related U.S. Application Data

(60) Provisional application No. 62/410,760, filed on Oct. 20, 2016.

(51) Int. Cl.
| | |
|---|---|
| *C12N 5/071* | (2010.01) |
| *A61F 2/02* | (2006.01) |
| *A61K 35/39* | (2015.01) |
| *A61K 45/06* | (2006.01) |
| *A61L 27/38* | (2006.01) |
| *C12N 5/0775* | (2010.01) |
| *A61P 5/50* | (2006.01) |
| *C08F 220/14* | (2006.01) |
| *B33Y 80/00* | (2015.01) |
| *C08F 220/28* | (2006.01) |

(52) U.S. Cl.
CPC .............. *C12N 5/0677* (2013.01); *A61F 2/02* (2013.01); *A61K 35/39* (2013.01); *A61K 45/06* (2013.01); *A61L 27/3834* (2013.01); *A61L 27/3895* (2013.01); *A61P 5/50* (2018.01); *B33Y 80/00* (2014.12); *C08F 220/14* (2013.01); *C08F 220/28* (2013.01); *C12N 5/0662* (2013.01); *C12N 5/0676* (2013.01); *A61F 2/022* (2013.01); *A61F 2240/001* (2013.01); *C12N 2506/02* (2013.01); *C12N 2506/1369* (2013.01); *C12N 2506/1392* (2013.01); *C12N 2506/22* (2013.01); *C12N 2513/00* (2013.01); *C12N 2533/30* (2013.01)

(58) Field of Classification Search
CPC .................................................. C12N 5/0677
See application file for complete search history.

(56) References Cited

U.S. PATENT DOCUMENTS

| | | | |
|---|---|---|---|
| 8,110,213 B2 | 2/2012 | Mikos et al. | |
| 8,735,117 B2* | 5/2014 | Darling | A61L 27/38 435/177 |
| 8,735,154 B2 | 5/2014 | Berkland et al. | |
| 9,422,524 B2 | 8/2016 | Van Apeldoorn et al. | |

OTHER PUBLICATIONS

Billiet et al. Biomaterials, 2014, 35:49-62.*
Izadifar et al. Tissue Engineering: Part C, 2016, 22:pp. 1-16 as printed.*
Faulkner-Jones et al., Biofabrication, 2015, 7, pp. 1-13 as printed.*
Giraldo, J et al., "Enhancing Clinical Islet Transplantation through Tissue Engineering Strategies," J. Diabetes Sci. Technol., Sep. 2010, pp. 1238-1247, vol. 4, No. 5.
Pagliuca, F et al., "Generation of Functional Human Pancreatic Beta Cells In Vitro," Cell, Oct. 9, 2014, pp. 428-439, vol. 159, Elsevier Inc.

* cited by examiner

*Primary Examiner* — Bin Shen
(74) *Attorney, Agent, or Firm* — Polsinelli PC

(57) ABSTRACT

Disclosed herein is a 3D-printed, biocompatible macroporous device that houses stem cell derived β-cell (SC-β cell) clusters within a degradable fibrin gel. Cluster sizes are used that avoid severe hypoxia within 3D-printed devices and a microwell-based technique is used for resizing clusters within this range. 3D-printed devices may function for at least 12 weeks, are retrievable, and maintain structural integrity.

16 Claims, 21 Drawing Sheets
(18 of 21 Drawing Sheet(s) Filed in Color)
Specification includes a Sequence Listing.

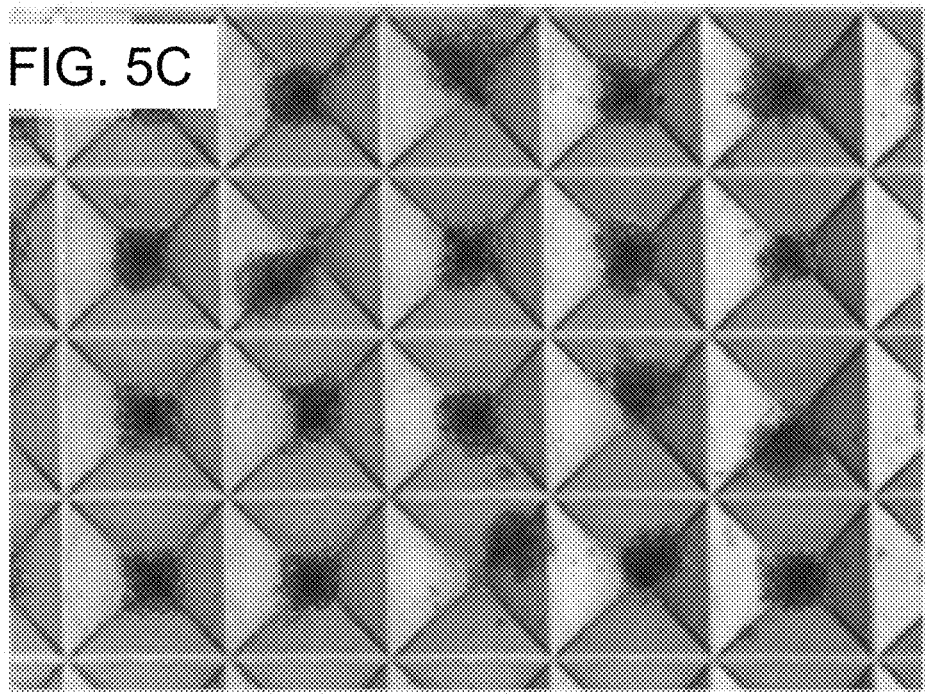
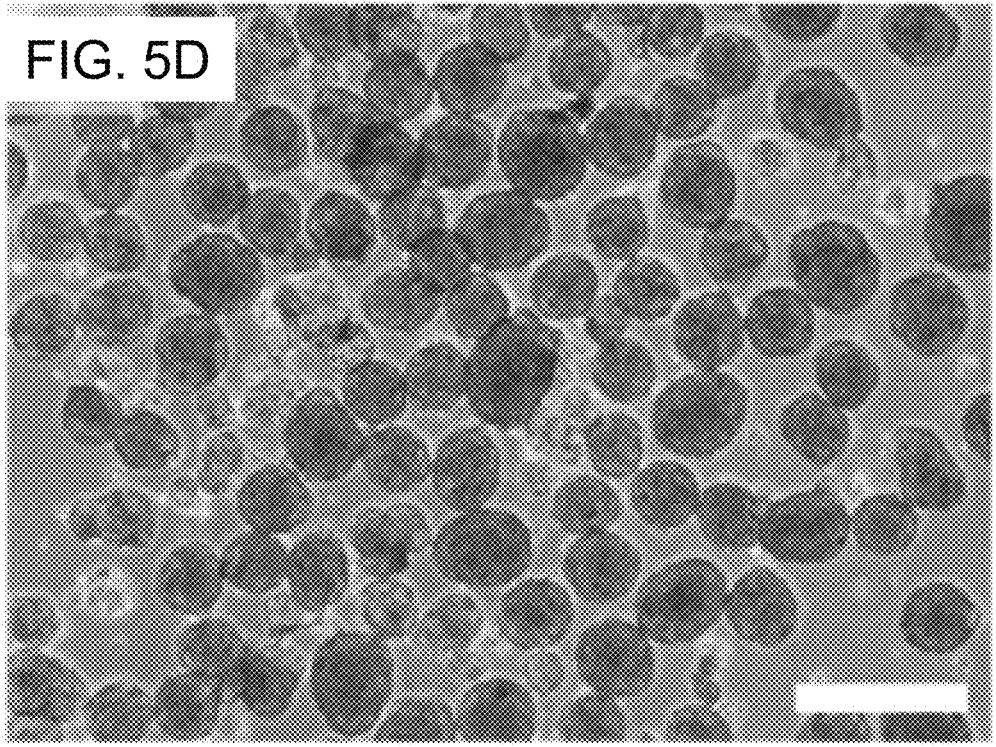

FIG. 10A
FIG. 10B
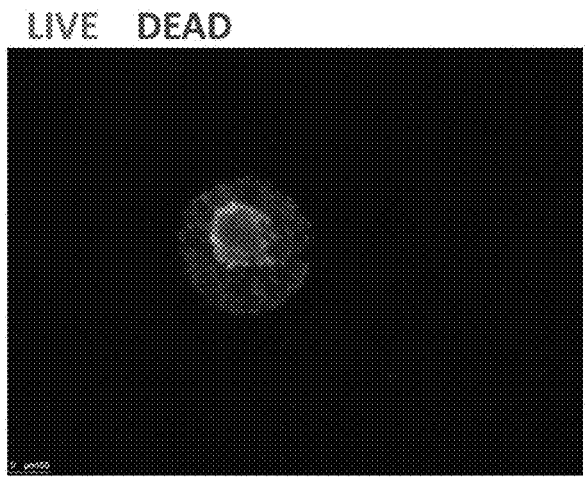
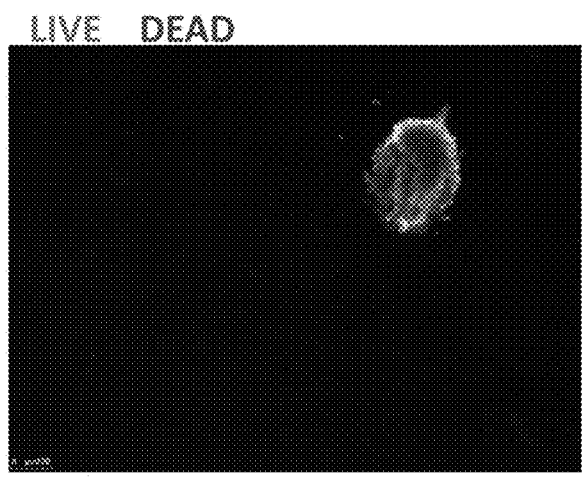
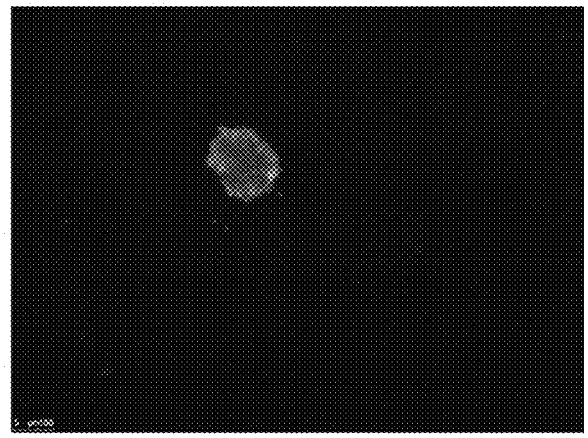
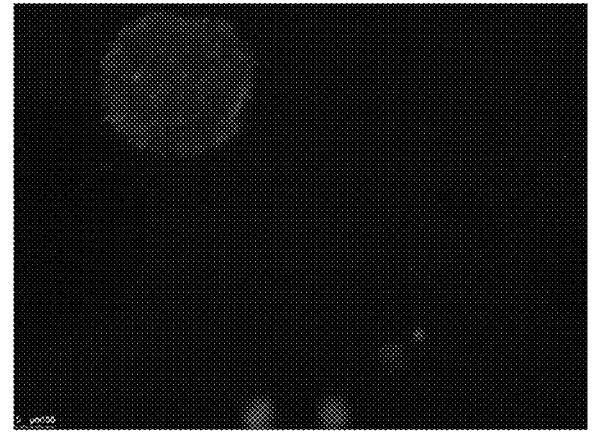
FIG. 10C
FIG. 10D

3D-PRINTED SCAFFOLD DEVICE FOR CELL TRANSPLANTATION

CROSS REFERENCE TO RELATED APPLICATIONS

This application claims priority to U.S. Provisional Application No. 62/410,760, filed on Oct. 20, 2016, the contents of which are entirely incorporated by reference herein.

GOVERNMENT SUPPORT

This invention was made with government support under DK020579 awarded by the National Institutes of Health. The government has certain rights in the invention.

FIELD

The present invention relates to cell-embedded, 3D printed scaffolds for tissue transplantation.

INCORPORATION OF SEQUENCE LISTING

A computer readable text file, entitled "047563-581606-Sequence-Listing_ST25.txt"created on or about Jun. 18, 2019,with a file size of about 2 KB contains the sequence listing for this application and is hereby incorporated by reference in its entirety.

BACKGROUND

Diabetes mellitus is a disease that affects hundreds of millions of people worldwide and is characterized by loss of blood glucose control. This typically occurs through either autoimmune-mediated destruction of insulin-producing β cells found in islets of Langerhans within the pancreas or insulin resistance in peripheral tissue that leads to β cell failure. Common treatments for diabetes include insulin injections or drugs that either increase insulin sensitivity or increase insulin secretion from remaining β cells, but complications due to imprecise glucose control persist and are costly.

Replacement of insulin-producing β cells using stem cells (SC-β cells) is a promising approach for controlling diabetes in patients. There are currently no FDA-approved treatments using human pluripotent stem cells (hPSC), and the safety of any such hPSC-based product needs to be assured, which can be achieved with removal of the transplanted cells. Transplantation of β cells benefits from the ability of the β cell to survive and function when transplanted in non-pancreatic locations. Most current clinical approaches with cadaveric islets rely on infusion into the liver, rendering them irretrievable. Other transplantation sites used in research, such as the kidney capsule or fat pad, are not viable for clinical transplantation. Large spaces, such as subcutaneous, intraperitoneal, or in the omentum, can potentially hold a sufficiently large cell-embedded device to convey a positive clinical outcome while also allowing for cell retrieval. Furthermore, much of the prior research has been focused on cellular encapsulation, which prevents vascularization of the transplanted graft, which causes cellular hypoxia, as oxygen is only delivered to the cells through diffusion, leading to either necrosis or greatly reduced function of transplanted islets.

Therefore, there is a need for a macroporous device that allows vascularization of the device, improving survival and function and reducing delays in glucose sensing, which is biocompatible and degradable, to further promote β cell survival and function along with host integration and vascularization.

SUMMARY OF INVENTION

The disclosure provides a 3D-printed device for transplanting cells into a patient.

Provided herein is a 3D-printed device for transplanting cells into a patient. The graft may include a 3D-printed biocompatible polymer having uniform pores, a plurality of cells implanted within the pores of the 3D-printed biocompatible polymer, and a degradable hydrogel surrounding the plurality of cells.

The plurality of cells in the transplantation graft may release a biologically active agent in response to a biological factor in the patient. The pores may be less than 200 µm in length or diameter. The length of the device may be between about 10 mm and about 25 mm. The width of the device may be between about 5 mm and about 10 mm. The thickness of the device may be between about 2 mm and about 5 mm. The biocompatible polymer may include polylactic acid (PLA), polycaprolactone, polyvinyl alcohol (PVA), gelatin methacrylate, or combinations thereof. The degradable hydrogel may include fibrin, collagen, alginate, triazole-thiomorpholine dioxide alginate, polyethylene glycol (PEG), PTFE, polyglycolic acid (PGA), poly-1-lactic acid (PLLA), polyhydroxyalkanoate, polycaprolactone-copolylactic acid, polylactide-coglycolide (PLGA), PDMS, polycaprolactone, gelatin methacrylate, or combinations thereof. The device may further include a coating layer, such as fibrin. The implanted cells may be selected from the group consisting of primary cells, pluripotent stem cells, differentiated stem cells, pancreatic cells, islet cells, β cells, thyroid cells, parathyroid cells, pituitary gland cells, adrenal gland cells, liver cells, genetically engineered cells, and any cell which secretes a biologically active agent. The implanted cells may be in a cluster, where each pore contains one cluster of cells.

Further provided herein is a method for transplanting cells into a patient. The method may include embedding a plurality of cells into a degradable hydrogel, implanting the degradable hydrogel with the plurality of cells into pores of a 3D-printed device, and implanting the 3D-printed device into the patient. The implanted cells may be in a cluster, where each pore contains one cluster of cells.

Also provided herein is a method of treating a patient in need thereof. The method may include implanting into the patient a 3D-printed device including a 3D-printed biocompatible polymer having uniform pores, a plurality of cells implanted within the pores of the 3D-printed biocompatible polymer, and a degradable hydrogel surrounding the plurality of cells. The plurality of cells in the 3D-printed device may release a biologically active agent in response to a biological factor in the patient.

The implanted cells may be selected from the group consisting of primary cells, pluripotent stem cells, differentiated stem cells, pancreatic cells, islet cells, β cells, thyroid cells, parathyroid cells, pituitary gland cells, adrenal gland cells, liver cells, genetically engineered cells, and any cell which secretes a biologically active agent. The implanted cells may be stem cell derived β cells. The biological factor may be selected from the group consisting of proteins, peptides, carbohydrates, polysaccharides, and any factor within the blood. The biological factor may be glucose. The biologically active agent may be selected from the group consisting of proteins, peptides, hormones, enzymes, and proteases. In an aspect, the biologically active agent may be insulin.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF DRAWINGS

The application file contains at least one drawing executed in color. Copies of this patent application publication with color drawing(s) will be provided by the Office upon request and payment of the necessary fee.

The description will be more fully understood with reference to the following figures and data graphs, which are presented as various embodiments of the disclosure and should not be construed as a complete recitation of the scope of the disclosure, wherein:

FIG. 5C shows reformed clusters after 24 hours of incubation in microwells.

FIG. 5D shows reformed clusters recovered from microwells.

FIG. 10A is a micrograph of a SC-β cell cluster stained with a LIVE/DEAD dye (green=alive, red=dead).

FIG. 10B is a micrograph of a SC-β cell cluster stained with a LIVE/DEAD dye (green=alive, red=dead).

FIG. 10C is a micrograph of a SC-β cell cluster stained with a LIVE/DEAD dye (green=alive, red=dead).

FIG. 10D is a micrograph of a SC-β cell cluster stained with a LIVE/DEAD dye (green=alive, red=dead).

DETAILED DESCRIPTION

Figure 1A:
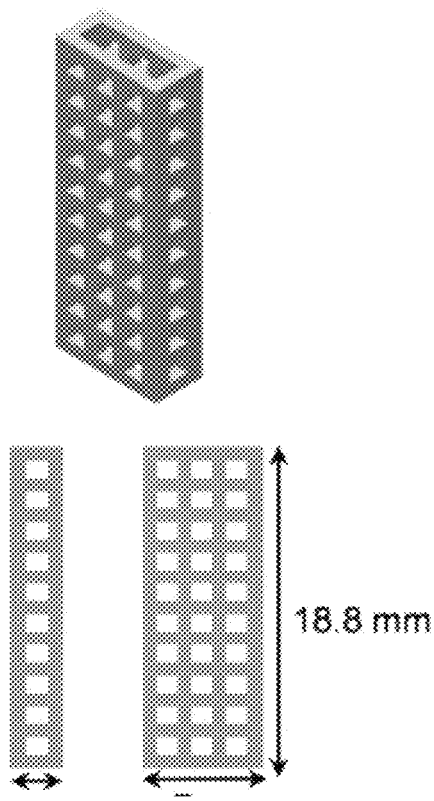
FIG. 1A is an image of a CAD design of a 3D printed device showing device dimensions, in one aspect.

The disclosure may be understood by reference to the following detailed description, taken in conjunction with the drawings as described below. It is noted that, for purposes of illustrative clarity, certain elements in various drawings may not be drawn to scale.

Replacement of insulin-producing β cells is a promising approach for controlling diabetes in patients. Transplantation of islets from cadaveric donors that contain β cells have been performed with patients via intrahepatic infusion and demonstrated improved blood glucose control over several years. Differentiation of hPSC has been used to generate SC-β cells in vitro from both human embryonic stem cells (hESC) and Type 1 diabetic patient-derived human induced pluripotent stem cells (hiPSC). These cells can be produced in almost unlimited quantities by suspension culture in spinner flasks, overcoming limitations in β cell supply from cadaveric islets, and have markedly similar characteristics compared to primary β cells, including gene expression and the ability to respond to glucose by secreting insulin both in vitro and in vivo. Importantly, transplanted SC-β cells control blood glucose in mouse models of diabetes. Transplantation of SC-β cells would benefit from a device that is retrievable and macroporous because of the large number of cells necessary to treat a diabetic patient.

Provided herein is a 3D-printed device for the subcutaneous transplantation of cells for cell replacement therapy. 3D printing provides the ability to rapidly create multiple devices in a relatively short period of time with a defined three-dimensional structure (FIG. 1). Recently, the cost of consumer-grade 3D printers has lowered such that the 3D-printed device may provide for a low-cost alternative to scaffold design. Devices with precise three-dimensional spatial configurations can be manufactured from low cost, biocompatible, and very slowly degrading materials. In an aspect, a low cost, consumer-grade 3D printer may be used to create the 3D-printed device by optimization of printing parameters and inclusion of a cooling step after each extruded layer that allows for fabrication of finer features, such as pores.

A major advantage of 3D printing is the ability to augment device designs with additional functionality that is not feasible with alternative approaches, such as solvent casting and particulate leaching with polydimethylsiloxane. 3D bioprinting has been previously used to plot islets within composite hydrogels, and while in vivo utility of this approach has not yet been demonstrated, such an approach could be combined with the 3D-printed device that is functional and retrievable while also providing encapsulation of cells to protect against immune attack. To minimize or eliminate time between transplantation and vascularization, pre-vascularized tissues could be used. Further functionality could be included in the device, such as anti-fibrotic materials or materials that release pro-angiogenic compounds.

The macroporous, retrievable 3D-printed device may provide for the subcutaneous transplantation of cells. In various aspects, the device may include implanted cells or may be void of cells. In an aspect, the cells may be organ-specific differentiated stem cells. A large number of biologically active, organ specific (e.g. pancreas, thyroid, adrenal gland) differentiated stem cells may be implanted into the device. The cells in the device may be any cell type in which there may be a need for transplanting into a host patient, such as an artificial organ, to replace a function in the body, or replace cells within the body. Non-limiting examples of cells which may be implanted into the 3D-printed device include primary cells, pluripotent stem cells, differentiated stem cells, pancreatic cells, islet cells, β cells, stem cell derived β-cells, cells specific to the thyroid, parathyroid, pituitary gland or adrenal gland, liver cells, genetically engineered cells, or any cell which secretes a biologically active agent. The cells may be mammalian or human cells. In one aspect, the implanted cells may be β cells derived from human pluripotent stem cells. In an aspect, the cells may be SC-β cells or cadaveric islets.

SC-β cells can be generated at a large scale in spinner flasks (>108 cells per flask), helping to overcome the shortage of cadaveric islets available for diabetes cell replacement therapy. These cells could potentially be genetically engineered to avoid immune destruction. SC-β cells can be derived from patient hiPSC to avoid allogeneic rejection. In situations of autoimmunity, which occurs in Type 1 diabetes, patient SC-β cells combined with an immunotherapy to selectively suppress autoimmunity is possible. Improvements in methodologies for generating SC-β cells in vitro will enable a consistent cell source that can be tailored to maximize transplantation outcomes, such as resizing of clusters to reduce hypoxia (FIG. 5). Furthermore, cadaveric islets could be substituted for SC-β cells and used with the 3D-printed device.

In various aspects, the cells may be pre-loaded into the 3D-printed device, loaded into the 3D-printed device after implantation of the device, and/or cells may be periodically loaded into the 3D-printed device as needed. In one aspect, the 3D-printed device may be seeded with cells prior to implantation in the patient. Additional cells may be periodically injected into the 3D-printed device to replace cells that may have died or left the device after implantation. The transplanted cellular concentration and volume is variable and may depend on the length or size of the device implanted in the host.

The device may be fabricated with a biocompatible polymer using a low cost, consumer-grade 3D printing. In an aspect, the biocompatible polymer may be polylactic acid (PLA), polycaprolactone, polyvinyl alcohol (PVA), gelatin methacrylate, or a biocompatible hydrogel.

In one aspect, the biocompatible polymer is PLA. PLA is biocompatible, has high retention of structural integrity, and is FDA approved for various bioengineering applications. PLA has a long degradation time, mechanical strength and retrievability can potentially be maintained for years. In addition, the low viscosity of PLA allows for it to be compatible with a broader range of 3D printers, including those that have limited extruder nozzle pressure.

In another aspect, the device may be fabricated from a hydrogel. In this aspect, the SC-β cell clusters may be mixed with the hydrogel prior to 3D printing. The hydrogel/SC-β cell cluster mixture may then be 3D bioprinted using a 3D printer, such that the cells are printed with the hydrogel. In some aspects, the hydrogel may be photopolymerized by UV light to solidify the hydrogel. In one aspect, the hydrogel may be gelatin methacrylate. SC-β cell clusters may then be mixed with the gelatin methacrylate, bioprinted, and cross-linked with UV light. There may or may not be a need to further fill the 3D printed device with separate hydrogel.

The length of the 3D-printed device may range from about 10 mm to about 25 mm. In various aspects, the length may range from about 10 mm to about 15 mm, from about 12 mm to about 17 mm, from about 15 mm to about 20 mm, from about 17 mm to about 22 mm, from about 20 mm to about 25 mm. In one aspect, the length of the device may be about 18.8 mm. The width of the 3D-printed device may range from about 5 mm to about 10 mm, from about 5 mm to about 7 mm, from about 6 mm to about 8 mm, from about 7 mm to about 9 mm, and from about 8 mm to about 10 mm. In one aspect, the width of the device may be about 7 mm. The thickness of the 3D-printed device may range from about 2 mm to about 5 mm, from about 2 mm to about 3 mm, from about 2.5 mm to about 3.5 mm, from about 3 mm to about 4 mm, from about 3.5 mm to about 4.5 mm, and from about 4 mm to about 5 mm. In one aspect, the thickness of the device may be about 3.2 mm.

The 3D-printed device may have pores throughout the device. The pores may be regular or irregular in shape. In various aspects, the pores may be square, rectangular, circular, oval, or any shape which may receive cells or a cluster of cells. The pores may have a length, width, and/or diameter ranging from about 50 μm to about 200 μm, from about 50 μm to about 100 μm, from about 75 μm to about 125 μm, from about 100 μm to about 150 μm, from about 125 μm to about 175 μm, and from about 150 μm to about 200 μm. In an aspect, the pores may have a diameter less than about 200 μm, less than about 150 μm, or less than 100 μm.

The pores may be loaded with cells for transplantation. In an aspect, SC-β cell clusters may be loaded into the pores of the 3D-printed device. The cells may be suspended in a degradable hydrogel to secure the cells within the pores of the 3D-printed device. In an aspect, the hydrogel may include, but is not limited to, fibrin, collagen, alginate, triazole-thiomorpholine dioxide alginate, polyethylene glycol (PEG), PTFE, polyglycolic acid (PGA), poly-1-lactic acid (PLLA), polyhydroxyalkanoate, polycaprolactone-co-polylactic acid, polylactide-coglycolide (PLGA), PDMS, polycaprolactone, gelatin methacrylate, any degradable hydrogel suitable for surrounding cells, and combinations thereof.

In one aspect, the hydrogel may be fibrin. In this aspect, the cells may first be mixed with fibrinogen, and thrombin may be added after the cell/fibrinogen mixture is added to the device, such that the fibrin hydrogel is formed within the device. In another aspect, the The degradable hydrogel may further include biologically active agents for protecting the cells implanted in the 3D-printed device from the patient's immune system. In other aspects, the degradable hydrogel may provide a physical barrier between the implanted cells and the patient's immune system.

Figure 3A:
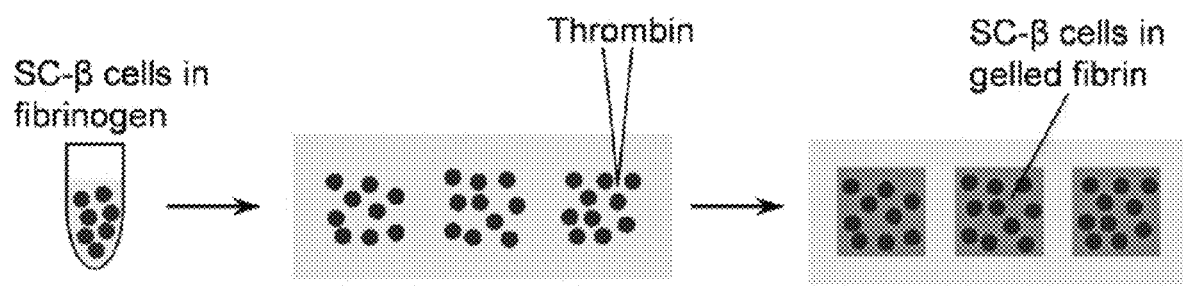
FIG. 3A is a schematic overview of cell loading process of SC-β cell clusters into 3D-printed device.

In one aspect, finite element modeling of oxygen diffusion-consumption (FIG. 4) may be used in combination with cluster resizing (FIG. 5) and a degradable fibrin gel (FIG. 3) to reduce hypoxia and promote vascularization. Using finite element modeling, it was calculated that cluster sizes smaller than about 171 μm in diameter would avoid severe transient hypoxia that would occur after transplantation but before vascularization. Using an in vitro test setup that leveraged the high oxygen permeability of silicone rubber, it was validated that resized clusters embedded within devices at physiological oxygen survive, consistent with the predictions of the finite element model. A microwell-based approach was developed for resizing SC-β cell clusters within the cluster size range that would prevent severe transient hypoxia with a finite element model of oxygen diffusion-consumption.

In various aspects, resized clusters of SC-β cells may have a diameter of less than about 171 μm, less than about 160 μm, less than about 150 μm, less than about 140 μm, less than about 130 μm, less than about 120 μm, less than about 110 μm, or less than about 100 μm. The resized SC-β cell clusters may then be suspended in the degradable hydrogel prior to loading into the pores of the 3D printed device. In an aspect, the clusters may include about $5 \times 10^6$ cells. In other aspects, the clusters may include about $4 \times 10^6$ cells, about $4.5 \times 10^6$ cells, or about $5.5 \times 10^6$ cells.

In one aspect, SC-β cell clusters may be mixed with about 120 μl to about 180 μl of 10 mg/ml fibrinogen. This mixture may then be loaded into the device, which may have a sealing film surrounding the pores of the device. After the loading of the mixture into the device, about 20 μl to about 60 μl of 50 IU/ml thrombin may be added to the fibrinogen-SC-β cell cluster mixture inside the device. The cell-loaded device may then be incubated at room temperature for about 3 minutes and moved to a 37° C. incubator for additional 10 min of incubation. The sealing film may then be removed from the device using sterile forceps.

The 3D-printed devices seeded with resized β cell clusters are functional, secreting insulin in response to a glucose injection. During transplantation, the devices may maintain their structural integrity and are retrievable. In various aspects, transplanted 3D-printed devices may be functional and retrievable for at least 2 weeks, at least 6 weeks, at least 12 weeks, at least 24 weeks, at least 36 weeks, at least 1 year, at least 2 years, or at least 5 years. FIGS. 8A-8F demonstrates that the device is retrievable for at least 12 weeks after transplantation. Since PLA has a long degradation time, mechanical strength and retrievability may be maintained for years.

The transplanted cells may secrete a biologically active agent. In an aspect, the biologically active agent may be secreted from the cell in response to a biological factor in the patient. The biological factor may include, but is not limited to, proteins, peptides, carbohydrates, polysaccharides, and any factor circulating within the patient's blood. In one aspect, the biological factor may be glucose or insulin.

The biologically active agent secreted from the implanted cells may affect a process or function in the body of the patient. In other aspects, the transplanted cells may absorb or consume a biological factor. In various aspects, the biologically active agent may include, but is not limited to proteins, peptides, hormones, enzymes, proteases, or any biologically active agent that may be secreted from the implanted cell. In one aspect, the biologically active agent may be insulin. In other aspects, the biologically active agent may be pancreatic hormones, thyroid hormones, parathyroid hormones, pituitary hormones, neuronal hormones, endocrine hormones, and other exocrine hormones. Other biologically active agents may include growth factors, essential and nonessential enzymes, and biologically active synthetic proteins. In one aspect, the biological factor may be glucose and the biologically active agent may be insulin. In this example, transplanted β cells may sense the amount of glucose in the blood and secrete insulin at an appropriate rate in response to the amount of glucose detected.

A 3D-printed device may be impregnated with insulin-producing pancreatic β cells for the treatment of Type 1 diabetes. A 3D-printed device including β cells may replace the need for a patient to take insulin. In an aspect, insulin-secreting pancreatic β cells may be produced from stem cells. The insulin-secreting pancreatic β cells may be able to sense glucose and deliver insulin.

In one aspect, the device may be removed from the patient after a period of time, thus allowing complete retrieval of transplanted cells to ensure patient safety. In this aspect, the device may be periodically replaced with a fresh device. In another aspect, the device may remain in the patient after transplantation.

Further provided herein is a method for transplanting cells into a patient. The method includes encapsulating a plurality of cells in a degradable hydrogel, filling the pores of a 3D-printed device with the degradable hydrogel containing the plurality of cells, and implanting the 3D-printed device into the patient.

Also provided herein is a method of treating a patient in need thereof. The method may include implanting a 3D-printed device into the patient, where a plurality of cells in the device release a biologically active agent in response to a biological factor in the patient. The implanted cells may be selected from pluripotent stem cells, differentiated stem cells, pancreatic cells, islet cells, β cells, stem cell derived β-cells, thyroid cells, parathyroid cells, pituitary gland cells, and adrenal gland cells. In an aspect, the implanted cells may be stem cell derived β cells. The biological factor may be selected from proteins, peptides, carbohydrates, polysaccharides, and any factor within the blood. In an aspect, the biological factor may be glucose. The biologically active agent may be selected from proteins, peptides, hormones, enzymes, and proteases. In an aspect, the biologically active agent may be insulin. The patient in need thereof may have diabetes.

EXAMPLES

Example 1

Modeling and 3D Printing of the Device

The computer-aided drafting (CAD) design of the scaffold was generated by utilizing the Autodesk Inventor software. The CAD design was then converted to a G-code format using the KISSlicer software. The following specifications of the 3D printer were selected for the generation of the device: 0.1 mm layer thickness, 0.2 mm extrusion width, 210° C.-220° C. extruder temperature, 60° C. printer bed temperature, 10 mm/s loop speed, 37.5 mm/s solid speed, 52.5 mm/s sparse speed, and the addition of a prime pillar. 1.75 mm natural PLA was used as the 3D printing filament and the single-extruder 3D printer Makergear M2 was utilized to manufacture the device.

Example 2

Stem Cell Culture and Differentiation of SC-β Cells

The Harvard University Embryonic Stem cell 8 line (HUES8) was utilized as the primary undifferentiated stem cell line for this experiment. The HUES8 cells were cultured using mTeSR1 in suspension culture inside 500 mL spinner flasks on a 9-Position stir plate at 70 rpm. Each passage occurred every three days with fresh media change 48 hours after the split with mTeSR1. During the passage, the HUES8 clusters were single-cell dispersed using 6 mL PBS and 6 mL Accutase for 6 min and were seeded at $6 \times 10^5$ cells/ml in mTeSR1 with 10 mM Y27632.

After 72 hours of culture in mTESR1, the following steps were followed to differentiate the HUES8 clusters into SC-β cell clusters. Media preparation for the differentiation protocol is as follows. S1 media was prepared with MCDB131 as the base media with 8 mM D-(+)-Glucose, 2.46 g/L NaHCO3, 2% FAF-BSA, 1:50,000 ITS-X, 2 mM Glutamax, 0.25 mM Vitamin C, and 1% Pen/Strep. S2 media was prepared with MCDB131.8 mM D-(+)-Glucose, 1.23 g/L NaHCO3, 2% FAF-BSA, 1:50,000 ITS-X, 2 mM Glutamax, 0.25 mM Vitamin C, and 1% Pen/Strep. S3 media was prepared with MCDB131.8 mM D-(+)-Glucose, 1.23 g/L NaHCO3, 2% FAF-BSA, 1:200 ITS-X, 2 mM Glutamax, 0.25 mM Vitamin C, and 1% Pen/Strep. S5 media was prepared with MCDB131.20 mM D-(+)-Glucose, 1.754 g/L NaHCO3, 2% FAF-BSA, 1:200 ITS-X, 2 mM Glutamax, 0.25 mM Vitamin C, 1% Pen/Strep, and 10 μg/ml Heparin (Sigma; H3149). S6 media was prepared with CMRL 1066 Supplemented (CMRLS) with 10% FBS, and 1% Pen/Strep. All prepared media were sterile filtered using top-bottom 0.22 μm filtration units.

For days 1 and 2 of the differentiation, S1 media with 100 ng/ml Activin A and 3 μM Chir99021 (only on day 1) were added. On days 4 and 5, S2 media with 50 ng/ml KGF was added. On day 7, S3 media with 10 μM Y27632, 50 ng/ml KGF, 0.25 μM Sant1 (Sigma; S4572), 2 μM Retinoic acid (RA) (Sigma; R2625), 200 nM LDN193189 (Sigma; SML0559), and 500 nM PdBU was added. On days 8, 9, and 11, S3 media with 10 μM Y27632, 5 ng/ml Activin A, 50 ng/ml KGF, 0.25 μM Sant1, and 100 nM RA was added. On days 13, 14, 16, and 18, S5 media with 0.25 μM Sant1, 100 nM RA, 1 μM XXI, 10 μM Alk5i II (Enzo Life Sciences; ALX-270-445), 1 μM L-3,3',5-Triiodothyronine (T3), 20 ng/ml Betacellulin were added. For days 20-34, S6 media with 10 μM Alk5i II and 1 mM T3 was fed every other day.

Example 3

Immunohistochemistry

Differentiated SC-β cell clusters were collected and fixed with 4% PFA at 4° C. overnight and embedded in Histo-Gel™ for histological sectioning. The paraffin embedded sectioned slides were washed with Histoclear and rehydrated. Antigen retrieval on the slides were performed by using 0.05M EDTA and put into pressure cooker for 2 hours. The slides were incubated in blocking solution (0.1% Triton-X and 5% donkey serum in PBS) for 30 min at RT. Primary antibodies were added and incubated at 4° C. overnight. Mouse anti-Nkx6.1 with 1:100 dilution, rat anti-insulin (pro-)/C-peptide with 1:300 dilution, and goat anti-human PDX-1/IPF1 with 1:300 dilution were used as primary antibodies for this assay. Secondary antibodies conjugated to Alexa Fluor 488 and 594 were used to detect the primary antibodies. The slides were then washed with blocking solution and incubated with secondary antibodies for 2 hours at RT. For collection of images, the slides were treated with Vectashield, covered with cover slides, and sealed with nail polish. Corresponding images were taken with the Leica DMI4000 fluorescence microscope. TUNEL assay was performed on select slides as part of the immunohistochemistry process, with quantitative analysis achieved via manual cell counting.

Example 4

Flow Cytometry

The SC-β cell clusters were dispersed into single-cell suspension by using 0.05% Trypsin-EDTA at 37° C. for 10-20 min. The single cells were centrifuged for 3 min at 300 rcf, followed by aspiration of the supernatant, and fixed in 4% PFA at 4° C. for 30 min. The cells were washed once with PBS and incubated in blocking solution for 1 hour at 4°

C. Primary antibodies in blocking solution were added to the cells and incubated overnight at 4° C. Mouse anti-Nkx6.1 with 1:100 dilution and rat anti-insulin (pro-)/C-peptide with 1:300 dilution were used as primary antibodies for this assay. After incubation, the cells were washed twice with blocking solution and incubated with secondary antibodies for 2 hours at 4° C. Secondary antibodies conjugated to Alexa Fluor 488 and 594 were used. Cells were then washed 3 times and resuspended in 500 μl-700 μl sorting buffer (0.5% BSA in PBS). The resuspended cells were filtered through a 40 μm nylon mash into flow cytometry tubes for analysis using the LSR-II flow cytometer. Quantification of the results was achieved with the FlowJo software.

Example 5

Encapsulating SC-β Cells Inside the Device

To encapsulate the SC-β cells inside the device, the 3D-printed devices were sprayed with 70% ethanol and dried inside a biosafety cabinet overnight. All five sides of the scaffold, except for the top side were wrapped with sealing film before the SC-β cell loading process. Fibrinogen from human plasma was reconstituted in CMRLS without FBS and Pen/Strep at RT to make up 10 mg/ml fibrinogen solutions. The aliquots were stored in the −80° C. Thrombin (Sigma) was reconstituted in PBS to make 50 IU/ml solution and was stored in −20° C.

The fibrinogen solution and thrombin solutions were thawed and equilibrated to RT before the cell-loading process. SC-β cell clusters (5×10$^6$ cells) mixed with 120 μl-180 μl of 10 mg/ml fibrinogen were manually loaded into the device with a P1000 tip. Immediately following, 20 μl-60 μl of 50 IU/ml thrombin was added to the fibrinogen-SC-β cell cluster mixture inside the device. The cell-loaded device was incubated at RT for 3 min and moved to 37° C. incubator for additional 10 min of incubation. The sealing film was then removed from the device using sterile forceps and the SC-β cell cluster loaded device was kept in S6 media until transplantation.

Example 6

Finite Element Modeling of Clusters within Hydrogel Slab

Steady-state oxygen concentration profiles were calculated using finite element modeling in COMSOL Multiphysics solving the species conservation equation $$D\alpha \nabla^2 pO_2 = \frac{V}{v_{cell}} \quad (1)$$

where D is the oxygen diffusivity coefficient (2.78×10-5 and 1.53×10-5 cm2/s for hydrogel and cells, respectively), a is the solubility coefficient (1.27×10-9 and 1.02×10-9 mol/cm3/mmHg for hydrogel and cells, respectively), pO2 is the local partial pressure of oxygen, V is cellular oxygen consumption rate, and $v_{cell}$ is the cellular volume (1817 μm$^3$/cell determined by manual counting). D and a for the hydrogel was assumed to be the same as culture medium. V was assumed to follow Michaelis-Menten kinetics, $$V = \frac{V_{max} pO_{2,cell}}{K_m + pO_{2,cell}} \quad (2)$$

where Vmax is maximal oxygen consumption (27.6 amol/cell/s, determined with a Seahorse XF24(3) analyzer), pO2, cell is the partial pressure of oxygen the cell is exposed to, and Km is the Michaelis-Menten constant (0.44 mmHg). The hydrogel slab was set at 5×5×1 mm, with the pO2 of the outer surface set at 40 mmHg. The inner cellular volume fraction within the slab was set and kept constant at 0.0956 to approximate that inside of the 3D-printed device while changing the number and size of clusters. The mesh was generated by setting the sequence type as physics controlled mesh and element size as finer. The calculation with 100 μm diameter clusters had 231 838 elements with an average quality of 0.6552, 123 μm diameter clusters had 123 344 elements with an average quality of 0.6511, 171 μm diameter clusters had 41 078 elements with an average quality of 0.6562, and 247 μm diameter clusters had 24 656 elements with an average quality of 0.6579.

Example 7

Resizing Clusters

Two types of Aggrewells, Aggrewell 400EX and Aggrewell 400, were utilized in the resizing process. 2 ml of the Rinsing solution was added to each well of the Aggrewell 400EX plate, and the plate was centrifuged at 2000 rcf for 5 min to remove any present bubbles. The rinsing solution was aspirated, and the plate was washed once with CMRLS and kept at RT. 2 ml of CMRLS was added to each well of the Aggrewell 400 plate, and the plate was centrifuged at 2000 rcf for 5 min and kept at RT until further usage.

The SC-β cell clusters between 25 days and 34 days in the SC-β cell differentiation protocol were utilized in the resizing process. The selected SC-β cell clusters were washed once with PBS and treated with TrypIE Express dispersion medium for 15 to 30 minutes. The cells were kept in the waterbath at 37° C. during the dispersion process. The cell count analysis was performed by the Vi-Cell automatic cell counter using the trypan blue dye exclusion method. The dispersed single cells in TrypIE Express were spun down at 300 rcf for 3 min and were washed once with CMRLS. The cells were then reconstituted in CMRLS+10 μM Alk5i II+1 μM T3. 14.1×106 cells and 3.6×106 cells were seeded onto each well of the Aggrewell 400EX and Aggrewell 400, respectively. The cell-loaded Aggrewell plates were then centrifuged at 300 rcf for 3 min and were incubated in the 37° C. incubator for 48 hours.

Example 8

Quantitative Reverse Transcription PCR

Gene expression was analyzed for both the resized (small) clusters and the large clusters 28 days into the differentiation protocol. The small clusters were collected for RNA extraction 48 hours after the resizing procedure. Total RNA was extracted using the RNeasy Mini Kit including the optional step of on-column DNase Digestion using the RNase-Free DNase set. The extracted RNA was reverse-transcribed using the High Capacity Reverse Transcription Kit. Amplification of the cDNA via StepOne Plus Real-Time PCR was performed using PowerUP SYBR Green Master Mix and the following custom primers from Invitrogen were used (gene, right primer sequence, and left primer sequence): Insulin (INS), 5'-CAATGCCACGCTTCTGC-3' (SEQ ID NO. 1), 5'-TTCTACACAC CCAAGACCCG-3' (SEQ ID NO. 2);

NKX6-1, 5'-CCGAGTCCTGC TTCTTCTTG-3' (SEQ ID NO. 3), 5'-ATTCGTTGGGGATGACAGA G-3' (SEQ ID NO. 4); PDX1, 5'-CGTCCGCTTGTTCTCCTC-3' (SEQ ID NO. 5), 5'-CCTTTCCCATGGATGAAGTC-3' (SEQ ID NO. 6); Chromogranin A (CHGA), 5'-TGACCTCAACGATG-CATTTC3' (SEQ ID NO. 7), 5'-CTGTCCTGGCTCTTCT-GCTC-3' (SEQ ID NO. 8); TBP (housekeeping gene), 5'-GCCATAAGGCATCATTG-GAC-3' (SEQ ID NO 9), 5'-AACAACAGCCTGCCACCTTA-3' (SEQ ID NO. 10). Data were analyzed using the $\Delta\Delta CT$ method and normalized to the large clusters.

Example 9

In Vitro Glucose-Stimulated Insulin Secretion

In vitro glucose stimulated insulin secretion was used to measure the in vitro function of large and small clusters. Krebs buffer (Krb) was formulated as follows: 128 mM NaCl, 5 mM KCl, 2.7 mM CaCl2, 1.2 mM MgCl2, 1 mM Na2HPO4, 1.2 mM KH2PO4, 5 mM NaHCO3, 10 mM HEPES, 0.1% BSA in Milli-Q filtered water. Krb was pre-warmed to 37° C. before the experiment. Large and small clusters 25-35 days in the differentiation protocol were collected in 1.7 ml microcentrifuge tubes, washed twice with 1 ml of krb per tube, and underwent preincubation with 1 ml of 2 mM glucose in krb for 1 hour in a 37° C. incubator. The tube lids were kept open during all incubations to allow for air exchange. Following the preincubation, supernatant was removed, and the clusters were challenged with 1 ml of 2 mM glucose (low glucose) in krb. After 1 hour, 200 µl of supernatant was collected (low glucose sample). Remaining supernatant was removed, and the clusters were challenged with 1 ml of 20 mM glucose (high glucose) in krb for 1 hour in the incubator. At the end of the challenge, 200 µl of supernatant was collected (high glucose sample). The collected low glucose and the high glucose samples were processed for human insulin quantification using the Human Insulin ELISA kit and measured by an absorbance microplate reader at 450 nm. The insulin quantification was normalized via the Vi-Cell automated viable cell counter by single-cell dispersing the clusters with 0.05% Trypsin-EDTA.

Example 10

In Vitro Hypoxia Experiment

The bottom of 50-mL tubes was removed, a thin layer of adhesive applied to the edges, and a sheet of 0.005-in thick silicone rubber (non-reinforced vulcanized gloss/gloss) attached to the opening. After allowing the adhesive to set for 24 hours, the tubes were incubated with 70% ethanol for 24 hours, the ethanol solution removed, and then dried for 24 hours underneath a UV lamp in a biological safety cabinet. To evaluate SC-β cell clusters, $5 \times 10^6$ cells worth of clusters were plated onto silicone rubber as free floating clusters, embedded into 3D-printed devices, or embedded as resized clusters in 3D-printed devices cultured in CMRLS+10 µM Alk5i II+1 µM T3, then placed in an humidified HERA-CELL V105 160i incubator set for 5.3% oxygen, 5% carbon dioxide, and the balance nitrogen. After 48 hours, cells were removed and assessed using the Live/Dead Viability/Cytotoxicity Kit and by fixation for histological examination.

Example 11

Transplantation

All in vivo experiments were performed in accordance with the guidelines of the relevant committee. Immunocompromised Fox Chase SCID Beige mice aged 10-12 weeks were obtained from Charles River and transplanted subcutaneously into the left flank with regular SC-β cell cluster-loaded devices as well as resized SC-β cell cluster-loaded devices.

Example 12

In Vivo Glucose-Stimulated Insulin Secretion

At 2 week and 12 week time points, the mice underwent in vivo glucose stimulated insulin secretion for quantitative measurement of human insulin level. The mice were fasted for 16 hours overnight before being injected intraperitoneal (IP) with 2 g D-(+)-glucose/1 kg body weight. At 0 and 30 minutes post injection, blood glucose was measured and blood was collected from the mice through facial vein puncture using a lancet. Serum was separated from the collected blood sample using Microvettes for quantification of serum human insulin level. The quantification was processed using the Human Insulin ELISA kit and measured by an absorbance microplate reader at 450 nm.

Example 13

Retrieval of the 3D Printed Device

The 3D printed device was removed from the host and incubated in 0.1 Triton-X solution at RT on a rotator for 1 week. After 1 week, the device was removed from the solution, and the remaining tissue inside the device was manually removed through the usage of syringe needles and pipets.

Example 14

3D Printer Optimization and Device Manufacture

The parameters of a MakerGear M2 3D printer were optimized to produce the small transplantation devices used in this study. These devices were designed using Autodesk Inventor and printed vertically utilizing the fused deposition modeling technique, an additive manufacturing technology (FIG. 1A). The printer utilized PLA as the feedstock material by increasing the nozzle temperature of the extruder nozzle to the melting temperature of PLA. The extruded PLA was then printed layer-by-layer, gradually increasing in height over the printing period. The devices were fabricated from PLA due to its biocompatibility and compatibility with the MakerGear M2 in contrast with other printer-compatible materials, such as acrylonitrile butadiene styrene (ABS), which is not biocompatible and thus not suitable for working with SC-β cells.

A range of extrusion speeds and temperatures were explored to produce consistent devices while minimizing the z-axis resolution (Table 1).

TABLE 1

3D printer parameters used in study.

| 3D-printing specification | Range |
| --- | --- |
| Layer thickness | 0.1 mm-0.3 mm |
| Extrusion width | 0.1 mm-0.5 mm |
| Support | None/Prime pillar |
| Extruder temperature PLA | 160° C.-220° C. |
| Bed temperature | 25° C.-70° C. |
| Loop speed | 5 mm s$^{-1}$-15 mm s$^{-1}$ |
| Solid speed | 37.5 mm s$^{-1}$-60 mm s$^{-1}$ |

Figure 1B:
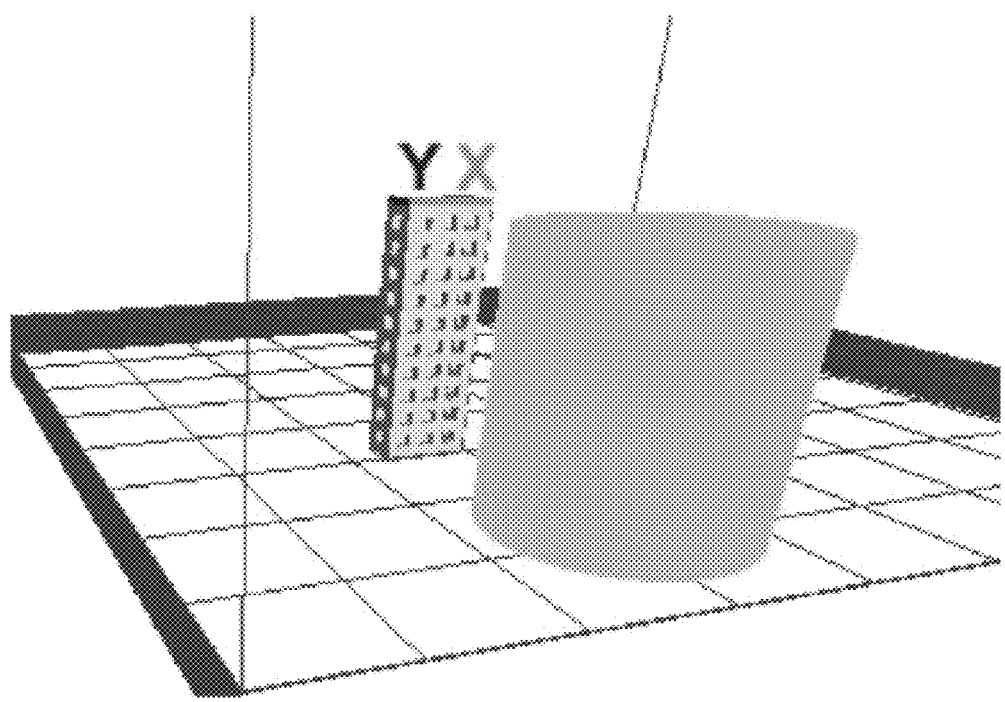
FIG. 1B is an image of the design in FIG. 1A converted to G-code format using KISSlicer showing device (grey) and prime pillar feature (orange).
Figure 1C:
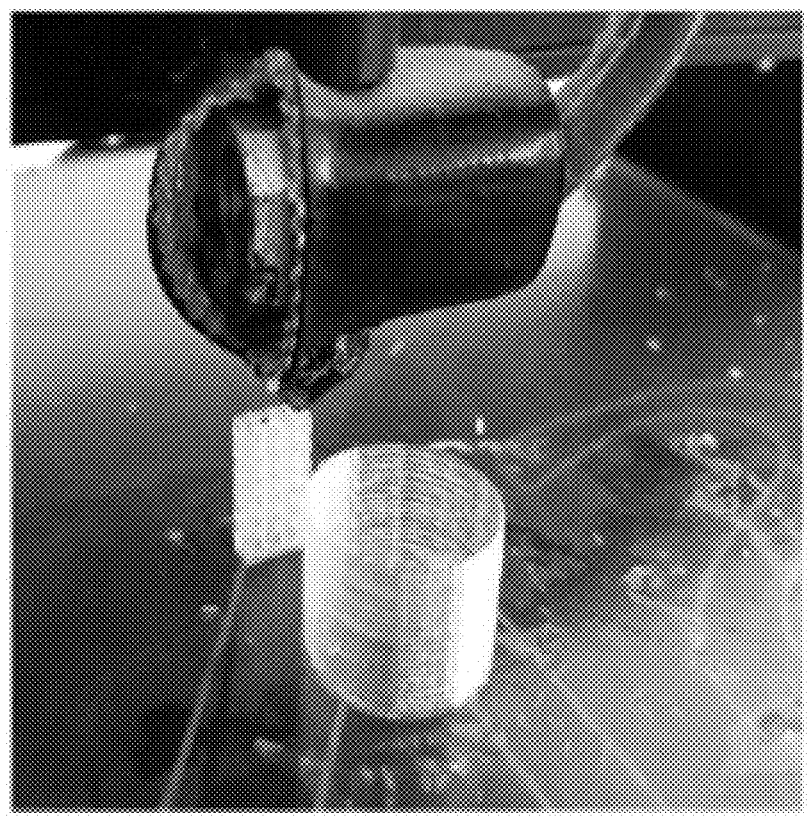
FIG. 1C is an image of a MakerGear M2 3D printing device and prime pillar.
Figure 1D:
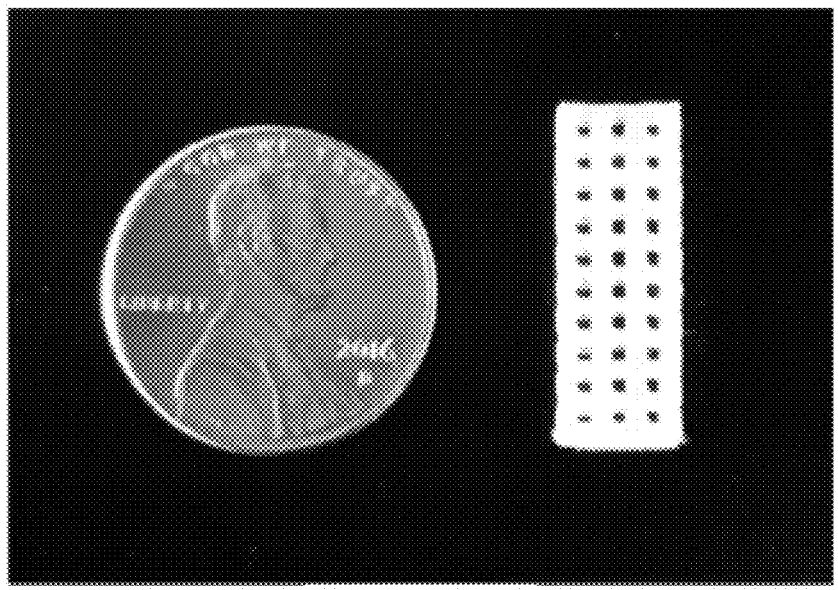
FIG. 1D is an image of a final 3D-printed device, in one aspect.

PLA with extruder temperatures lower than 200° C. did not produce consistent extrusion width, resulting in an uneven surface level during the first few layers of the device, which disrupted the printer from continuing with the subsequent layers. The precise control of the bed temperature was found to be critical for initiating the 3D printing process. Setting the bed temperature to the glass transition temperature (Tg) of PLA at 60° C. allowed for the extruded layers to adhere quicker to the glass bed of the 3D printer, providing a solid foundation. Due to the intrinsic melting point of PLA between 180° C.-210° C., the inclusion of a prime pillar feature (orange structure in FIG. 1B) in the 3D printing process may be necessary to increase the solidifying time for each layer of PLA, thereby maintaining the structural integrity of the device while minimizing stringing of unwanted PLA material (FIG. 1B-1D). The exclusion of the prime pillar resulted in buildup of PLA residue on the extruder tip, affecting the precision of the 3D printer. Each 3D-printed device weighed approximately 0.275 g. On a cost-per-weight basis, the material cost of manufacturing one device is approximately $0.01, enabling economic production of many devices.

Example 15

Production and Loading of SC-β Cells into 3D-Printed Device

Figure 2A:
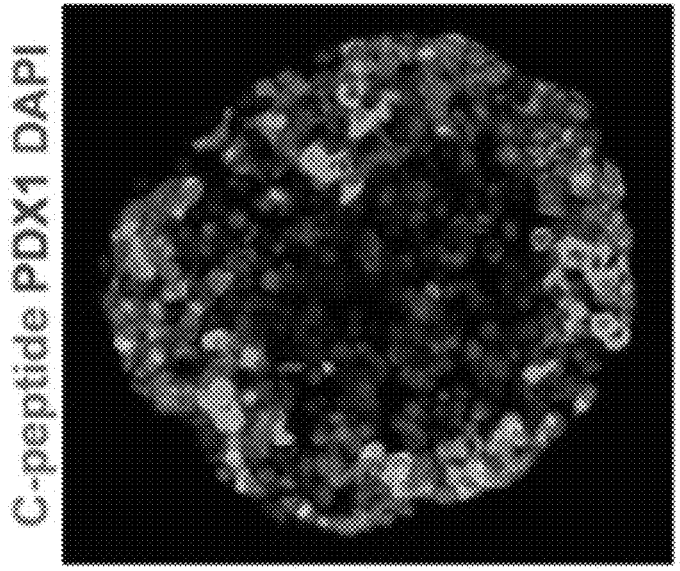
FIG. 2A is a histological section of SC-β cell clusters stained for C-peptide (green) and PDX1 (red) and with 4,6-diamidino-2-phenylindole (DAPI; blue).
Figure 2B:
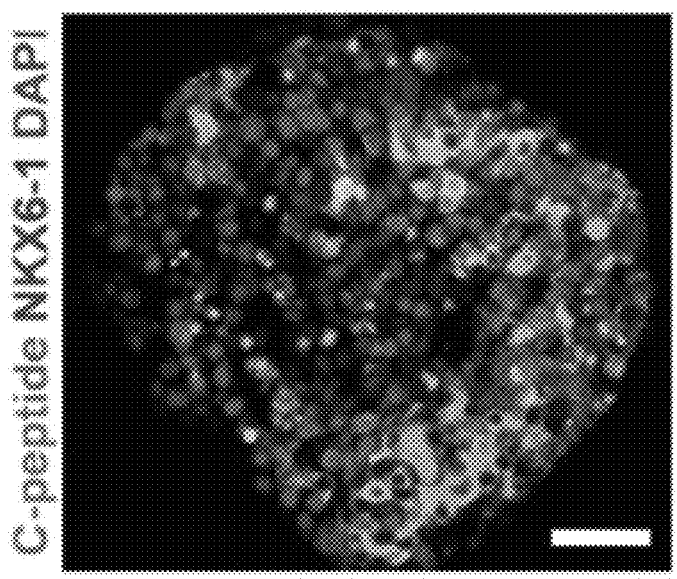
FIG. 2B is a histological section of SC-β cell clusters stained for C-peptide (green) and NKX6-1 (red) and with DAPI (blue).
Figure 2C:
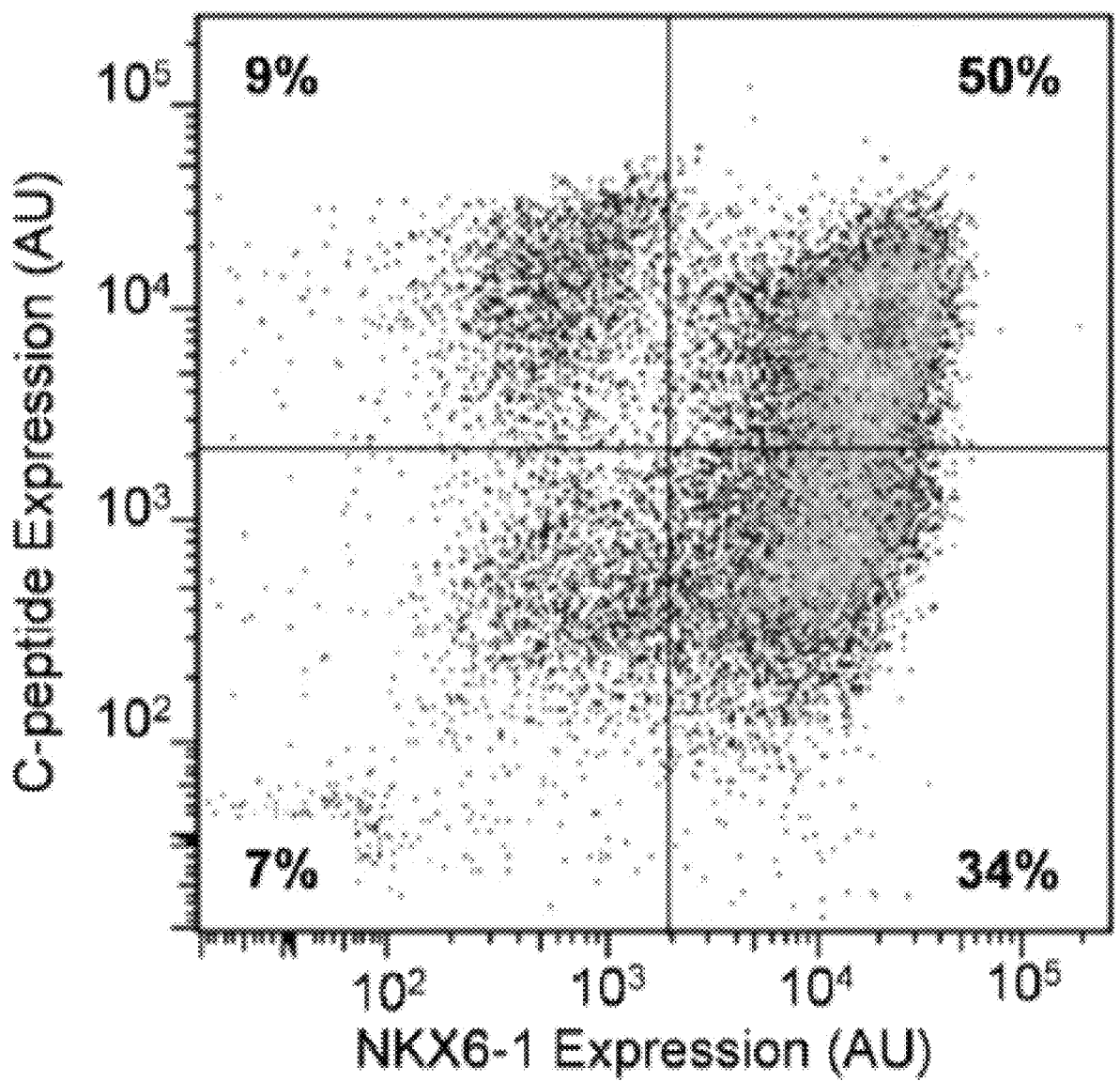
FIG. 2C is a flow cytometry dot plot of dispersed and fixed cells stained for C-peptide and NKX6-1. Scale bar=50 μm. Act A, activin A; Alk5i, Alk5 receptor inhibitor II; CHIR, CHIR9901; KGF, keratinocyte growth factor; LDN, LDN193189; PdbU, phorbol 12,13-dibutyrate; RA, retinoic acid; T3, triiodothyronine; Y, Y27632; AU, arbitrary units.

In order to generate SC-β cells to load into 3D-printed devices for transplantation, the HUES8 hESC line was differentiated using a directed differentiation protocol that utilizes a specific temporal combination of growth factors and small molecules to induce a β cell-like phenotype. Cells are cultured in suspension culture within spinner flasks in cellular aggregates consisting of >10$^3$ cells each to produce cells that co-express C-peptide, which is encoded by the insulin gene, with NKX6-1 and PDX1, transcription factors found in β cells (FIGS. 2A and 2B). Approximately 50% of cells express both C-peptide and NKX6-1, quantified with flow cytometric assessment of dispersed and immunostained cells (FIG. 2C).

Figure 3B:
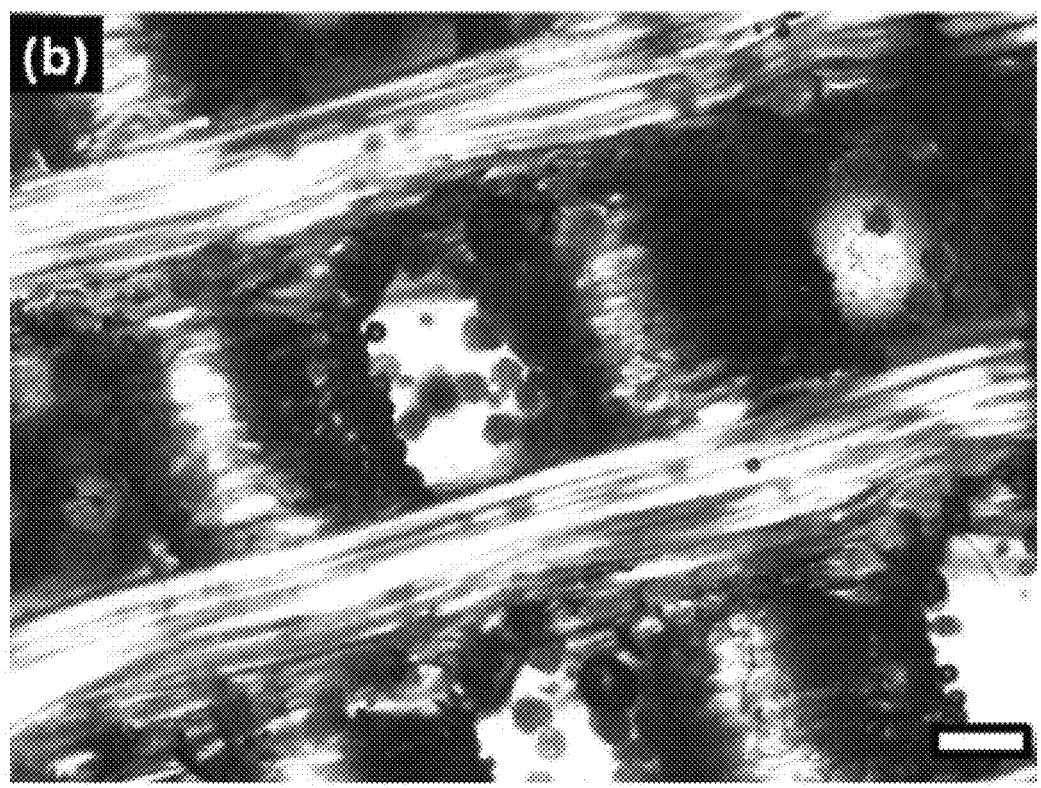
FIG. 3B is an image of fibrin-embedded clusters captured within 3D-printed device. Scale bar=500 μm.

In order to load and secure SC-β cell clusters within the 3D-printed devices (FIG. 3A), SC-β cell clusters (5×10$^6$ cells per mouse) were suspended in a fibrinogen solution and inserted into the device sealed with an ethanol-sterilized wrapping. Thrombin solution was immediately added directly into the cellular suspension within the device and manually shaken to maintain the cluster distribution. The gel cross-linked rapidly, being able to remain inside the device without the wrapping after 1-5 min (FIG. 3B). Maintaining the three-dimensional spatial distribution of clusters likely helps maximum cell viability by providing more uniform oxygenation inside the device.

Example 16

Finite Element Modeling of Clusters within Hydrogel

Figure 4:
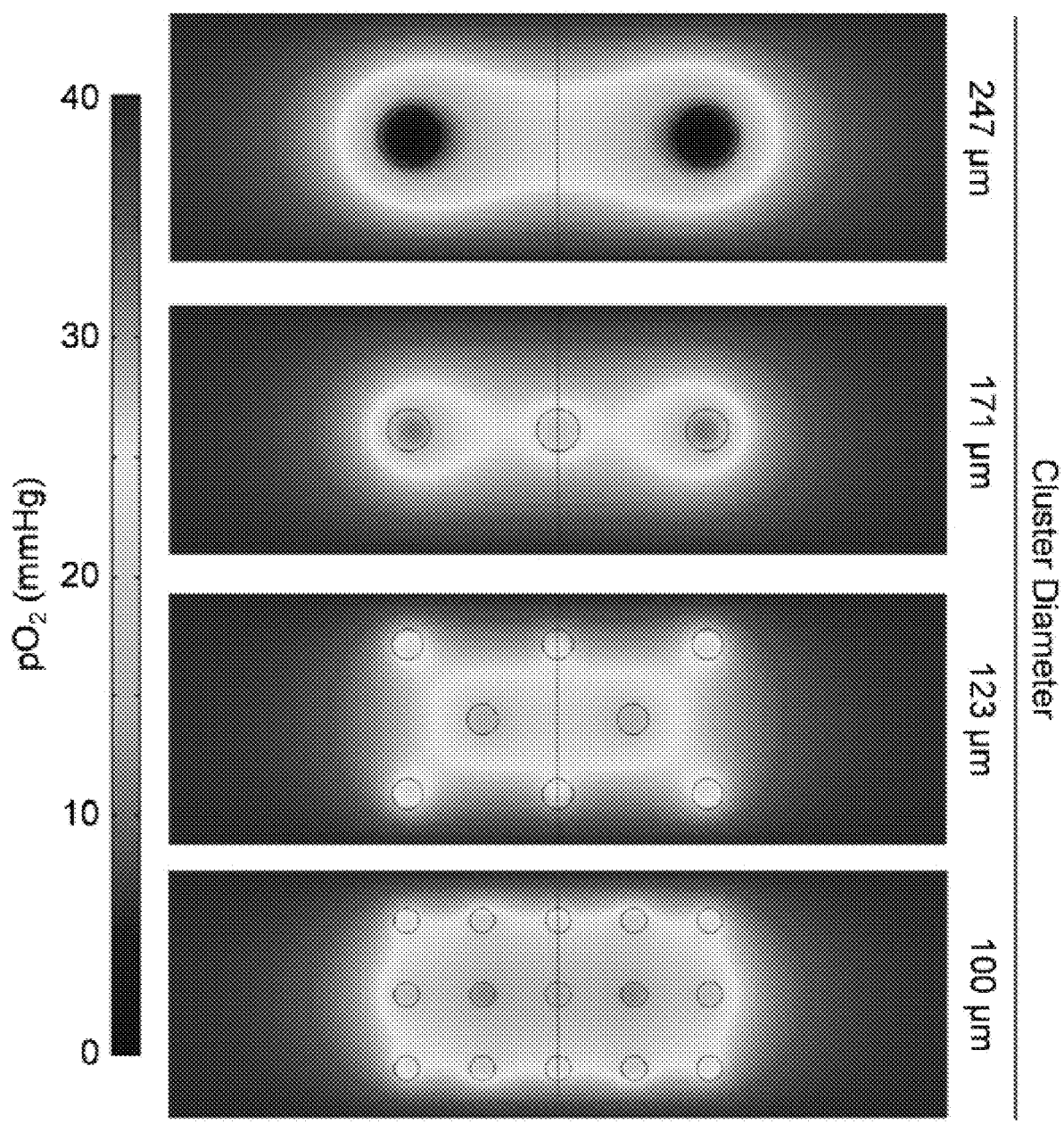
FIG. 4 is a finite element modeling of oxygen concentration within cluster-embedded hydrogel slab. Cluster sizes ranging from 100-247 μm in diameter were evaluated, maintaining the total cellular volume within a 1-mm thick slab.

Although the device design includes encapsulation of SC-β cell clusters within a fibrin gel, in part to promote vascularization, there may be a transient period before host vascularization into the device that the cells would be subjected to lower pO2. This was of particular concern in a scalable suspension stem cell culture system, as the cells are grown in large clusters that could be diffusion limiting for oxygen, and even low, non-zero, values of pO2 are known to reduce function in β cells. In order to evaluate this assumption, finite element modeling of oxygen consumption-diffusion of cells was performed within a hydrogel slab packaged into cluster sizes ranging from about 100-247 μm diameter, keeping total cellular volume constant (FIG. 4). This model assumed that the pO2 surrounding the hydrogel slab was 40 mmHg to approximate that found in the surrounding microvasculature. Large clusters sized 247 μm had severely low values of pO2 within the clusters, with many of the cells being exposed to virtually no oxygen. Smaller cluster sizes (100-171 μm) had much shallower gradients in pO2, with no cells approaching 0 mmHg. From this model, a range of cluster sizes that avoid severe hypoxia was established.

Example 17

Establishment of SC-β Cell Cluster Resizing Approach

Figure 5A:
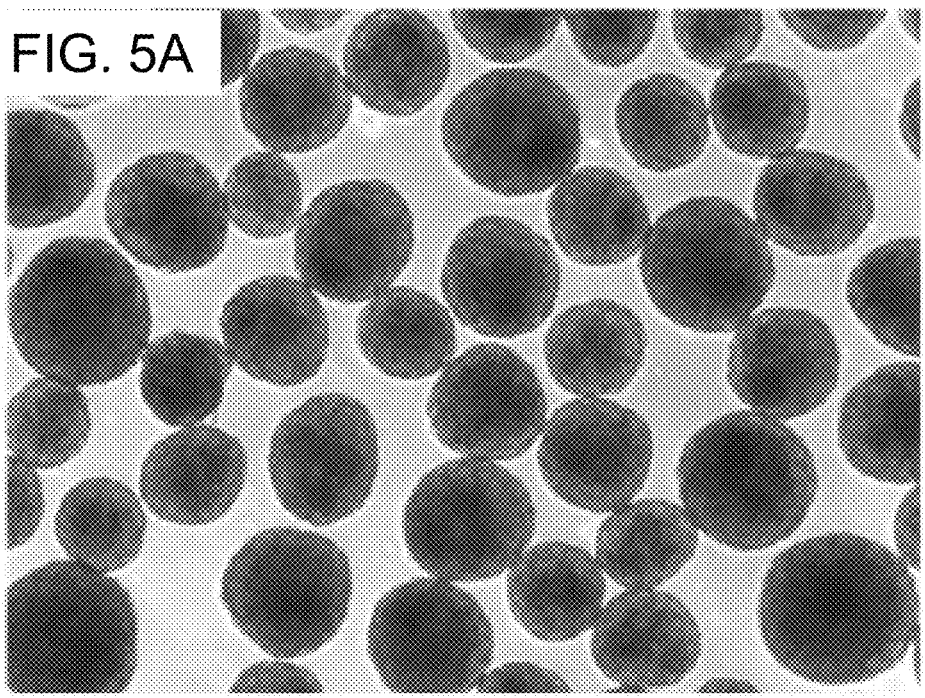
FIG. 5A shows SC-β cell clusters before dispersion.
Figure 5B:
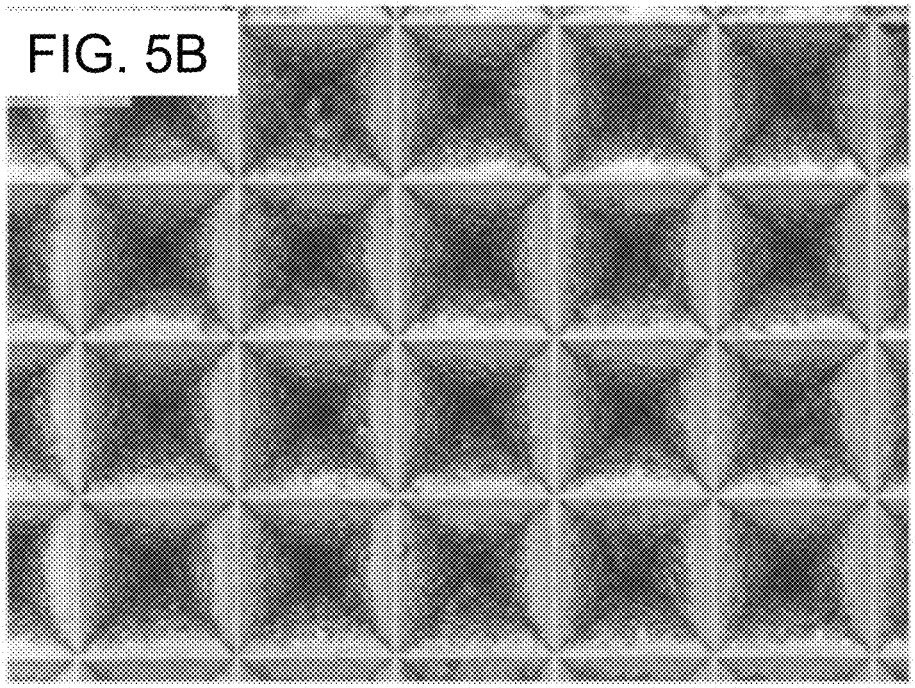
FIG. 5B shows clusters dispersed into a single-cell suspension and seeded into microwells.
Figure 5E:
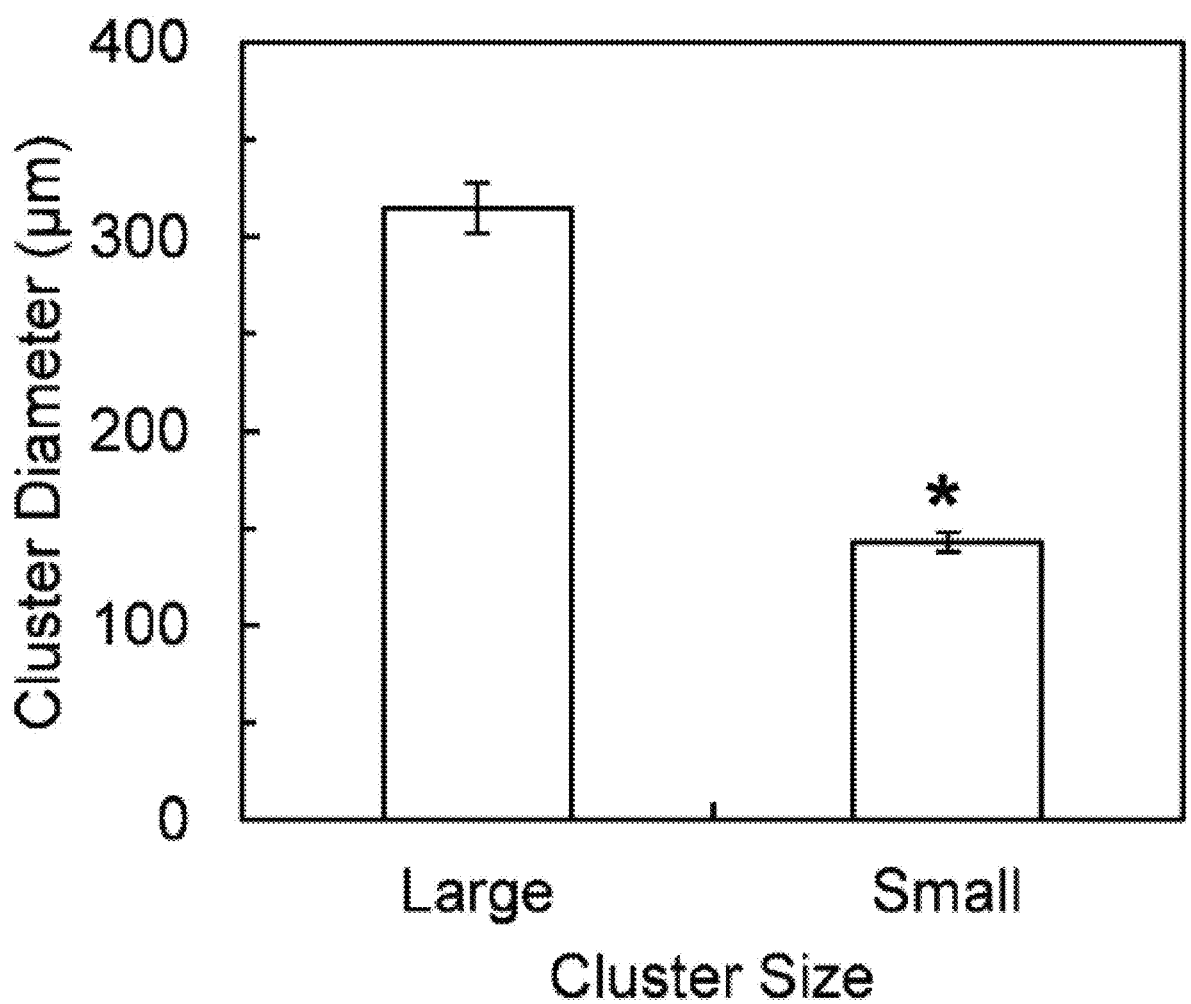
FIG. 5E shows measurement of average cluster diameter before (large) and after (small) resizing. n=40. Scale bar=400 μm. *p<0.01 (two-sided unpaired t-test).
Figure 5F:
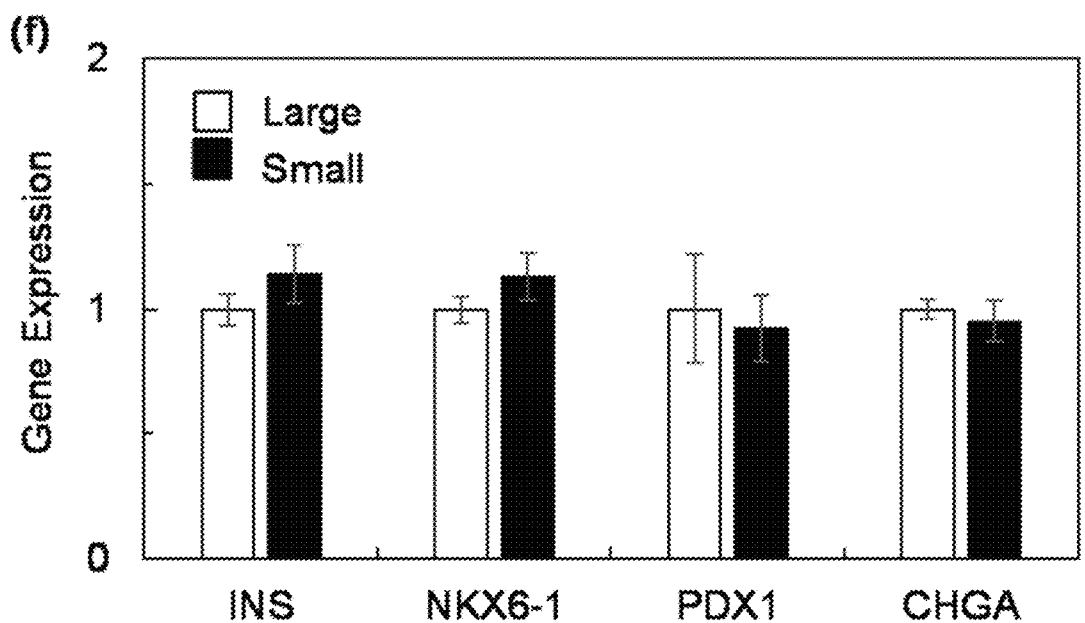
FIG. 5F shows gene expression of resized small clusters 28 days into the differentiation protocol relative to large clusters (n=4).
Figure 5G:
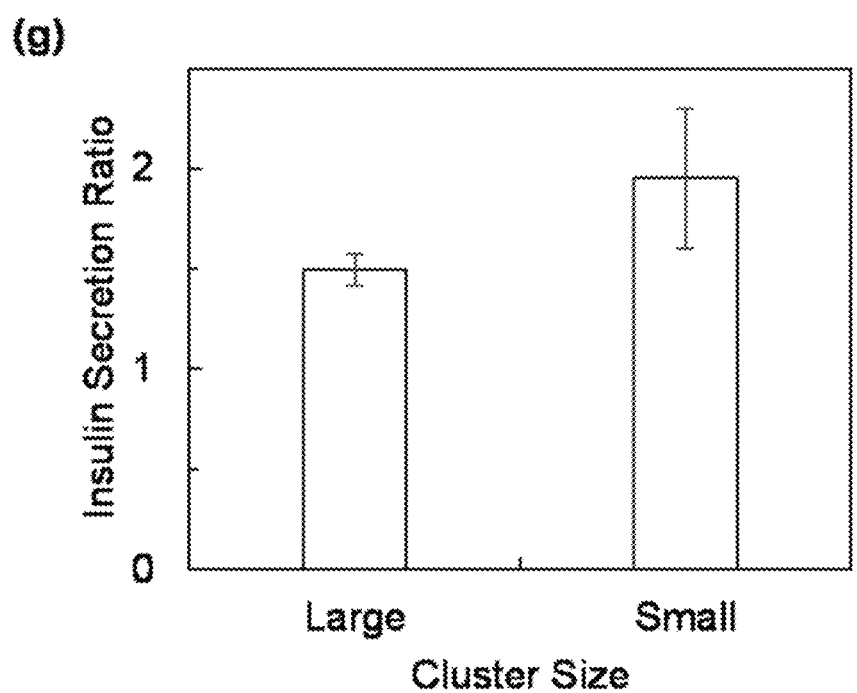
FIG. 5G shows a ratio of insulin secretion at high glucose over at low glucose for large and small SC-β cell clusters (n=3).

To avoid transient hypoxia within the 3D-printed device, an approach to resize SC-β cell clusters to smaller sizes that are within the 100-171 μm diameter range identified in the finite element model (FIG. 4) was established. Large SC-β cell clusters (FIG. 5A) were dispersed into a single-cell suspension, and seeded 3×10$^3$ cells per 400 μm microwell (FIG. 5B). After 48 hours, the cells reformed a small cluster (FIGS. 5C-5D), with the resized clusters averaging about 143±5 μm in diameter. The expression of the β cell genes insulin (INS), NKX6-1, PDX1, and chromogranin A (CHGA) was maintained (FIG. 5F), and the clusters were able to increase insulin secretion in response to high glucose (FIG. 5G).

Example 18

In Vitro Validation of Device Design

Figure 6:
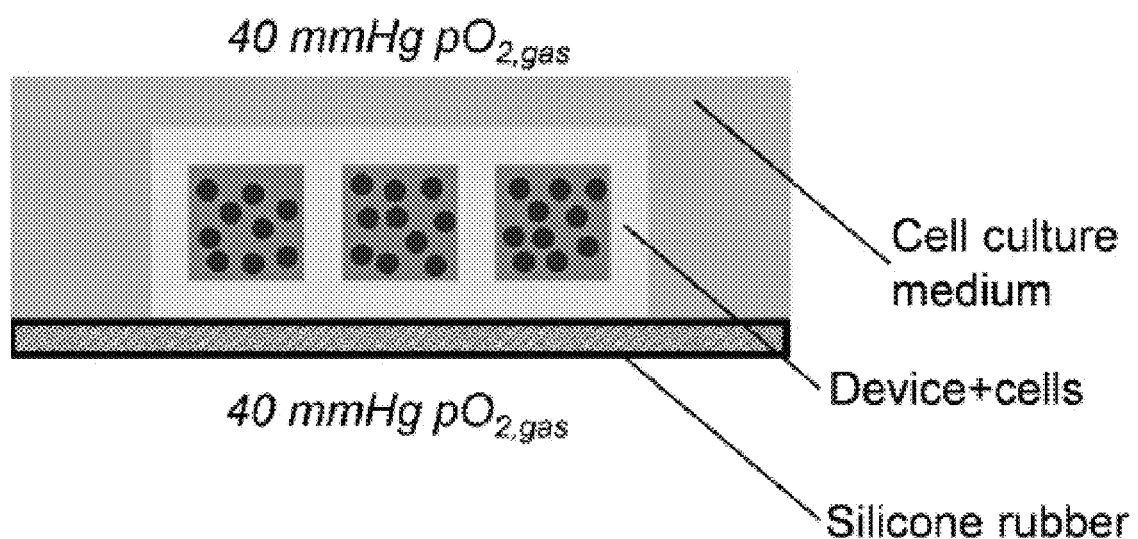
FIG. 6 is a schematic overview of in vitro culture system for testing devices at physiological oxygen.
Figure 7A:
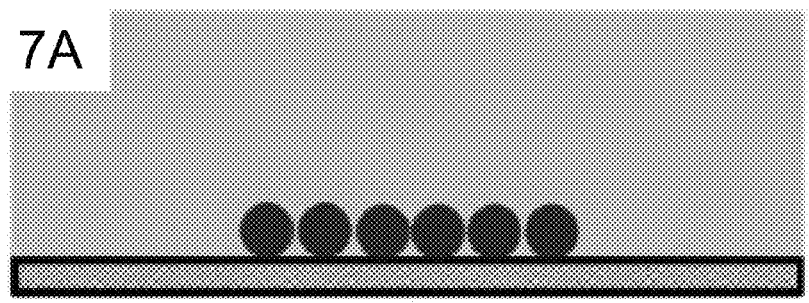
FIG. 7A is a schematic illustrating test set up for free floating large clusters.
Figure 7B:
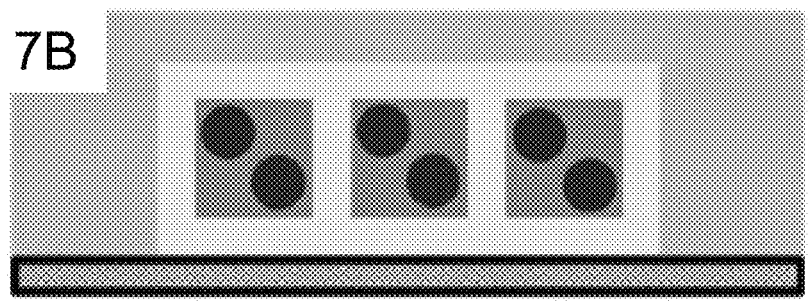
FIG. 7B is a schematic illustrating test set up for large clusters loaded into device.
Figure 7C:
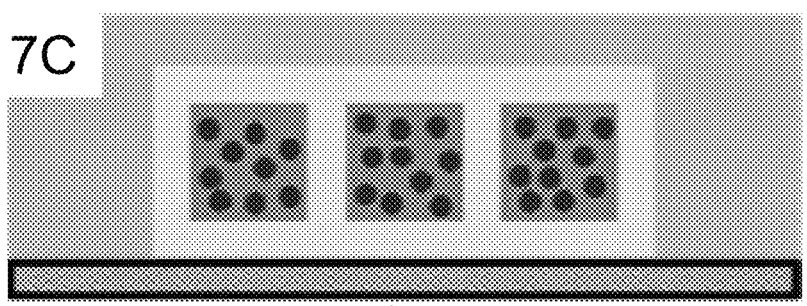
FIG. 7C is a schematic illustrating test set up for small clusters loaded into device.
Figure 7D:
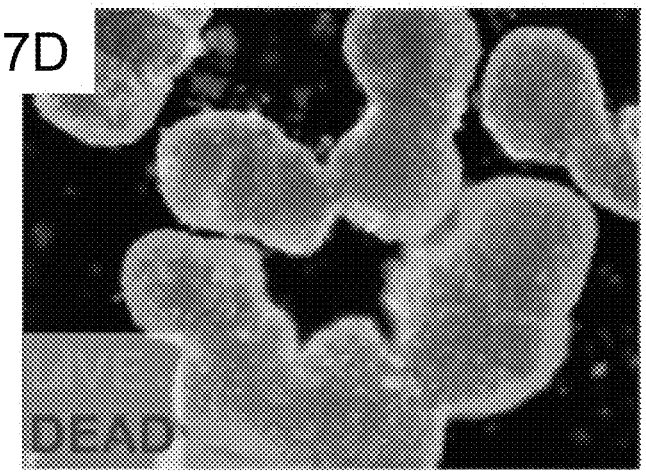
FIG. 7D shows an image of clusters stained with a fluorescent viability dye after 48 hours of culture at 40 mmHg pO2, gas cultured as indicated in FIG. 7A.
Figure 7E:
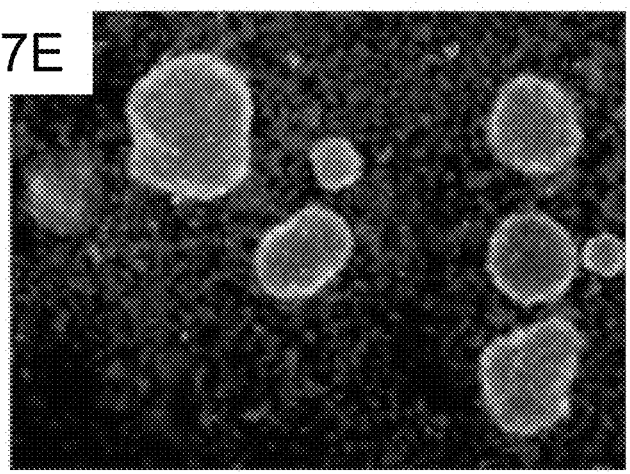
FIG. 7E shows an image of clusters stained with a fluorescent viability dye after 48 hours of culture at 40 mmHg pO2, gas cultured as indicated in FIG. 7B.
Figure 7F:
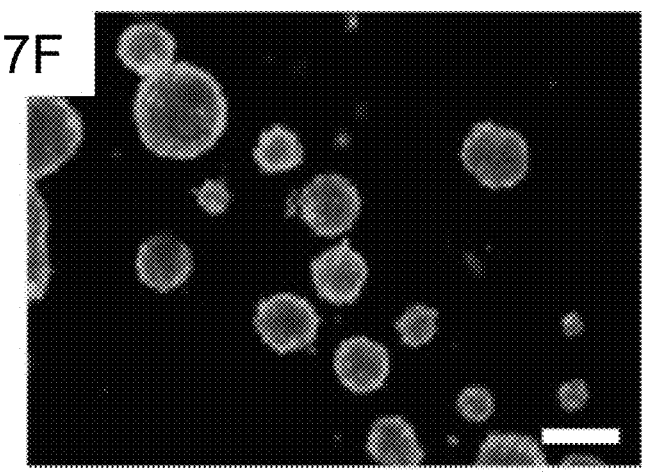
FIG. 7F shows an image of clusters stained with a fluorescent viability dye after 48 hours of culture at 40 mmHg pO2, gas cultured as indicated in FIG. 7C. Scale bar=200 μm
Figure 7G:
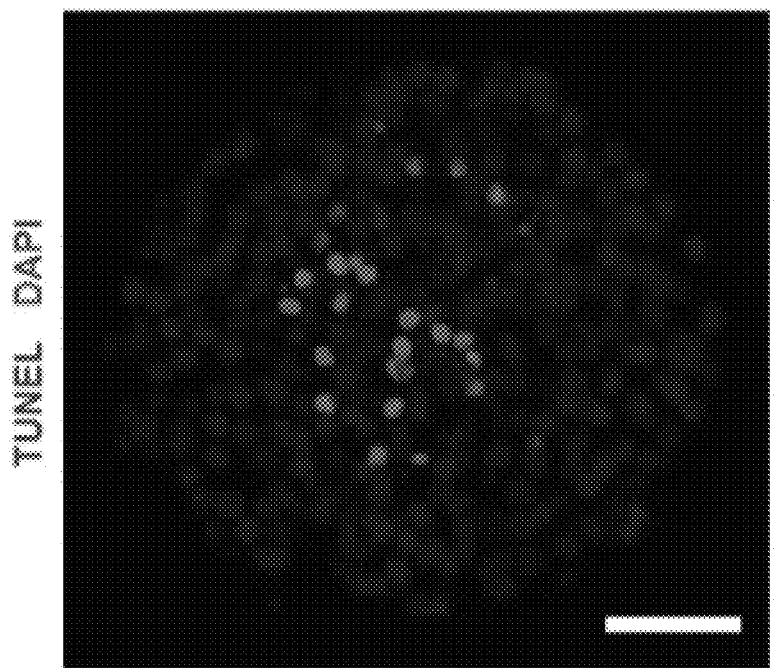
FIG. 7G is a histological section of SC-β cell clusters cultured as in FIG. 7B stained with a TUNEL assay (red) and with DAPI (blue). Scale bar=50 μm
Figure 7H:
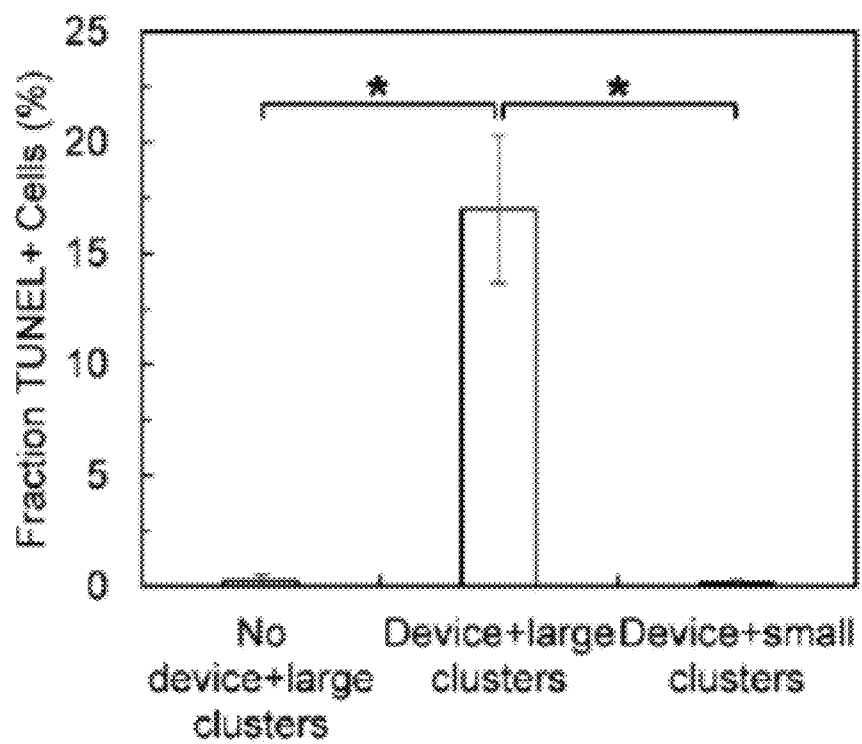
FIG. 7H is a quantitation of TUNEL+ cells from histological sections. *p<0.01 (two-sided unpaired t-test).

In order to further validate the findings of the mathematical model, an in vitro culture system was developed to test devices under defined values of pO2 comprised of a highly oxygen permeable silicone rubber surface on top of which devices or cell clusters can be cultured (FIG. 6). The oxygen permeability of the silicone rubber results in a minimal oxygen concentration gradient through the material, allowing for pO2 in the incubator to match that of the bottom surface of the device being tested. FIGS. 7A-7H show a resized cluster loaded into 3D-printed device is resistant to hypoxia-induced death. With this system, survival of SC-β cell clusters was evaluated not in a device (FIG. 7A), within the device (FIG. 7B), or resized into smaller clusters within the device (FIG. 7C) after 48 hours of culture at 40 mmHg pO2. After this acute culture, the cells were qualitatively assessed using a viability dye that stains membrane-permeable cells and observed substantial cell death for large clusters cultured within the device but not for the other two culture conditions (FIGS. 7D-7F). To further evaluate the SC-β cell clusters, the clusters were fixed, sectioned, and treated with a TUNEL assay to detect DNA fragmentation due to death and observed TUNEL+ cells within the central core of large clusters that were cultured within the device (FIG. 7G). When quantified, there were more TUNEL+ cells in large clusters within the device compared to large clusters not in a device or small clusters within the device (FIG. 7H). This in vitro assessment validates the prediction of the mathematical model that smaller clusters avoid severe hypoxia within the 3D-printed device.

Example 19

Transplantation of 3D-Printed Device Loaded with SC-β Cells

Figure 8A:
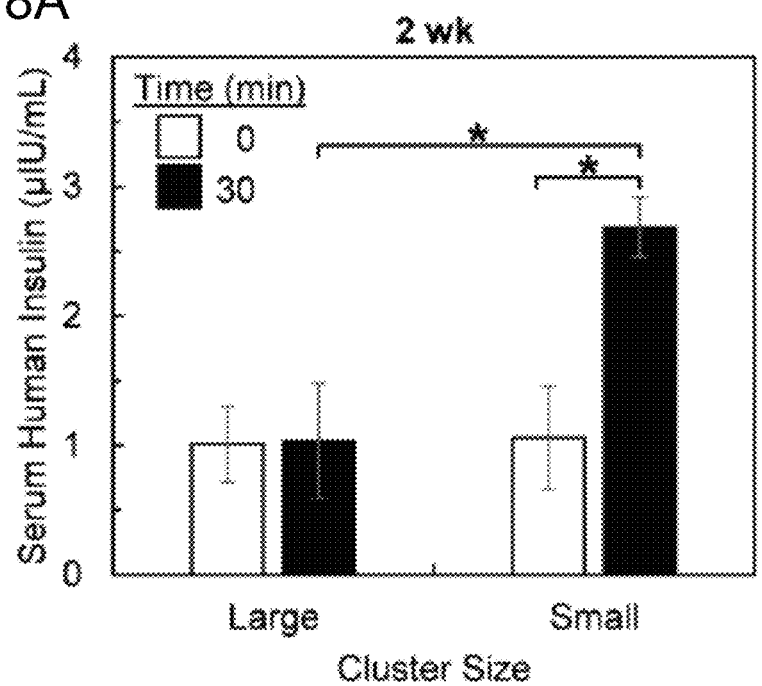
FIG. 8A shows an in vivo glucose stimulated insulin secretion assay of mice 2 weeks (n=6 for large clusters and n=7 for small clusters) after transplantation. Mice were fasted overnight and serum collected before (0 min) and 30 min after an intraperitoneal injection of glucose. Human insulin was quantified from this serum using ELISA.
Figure 8B:
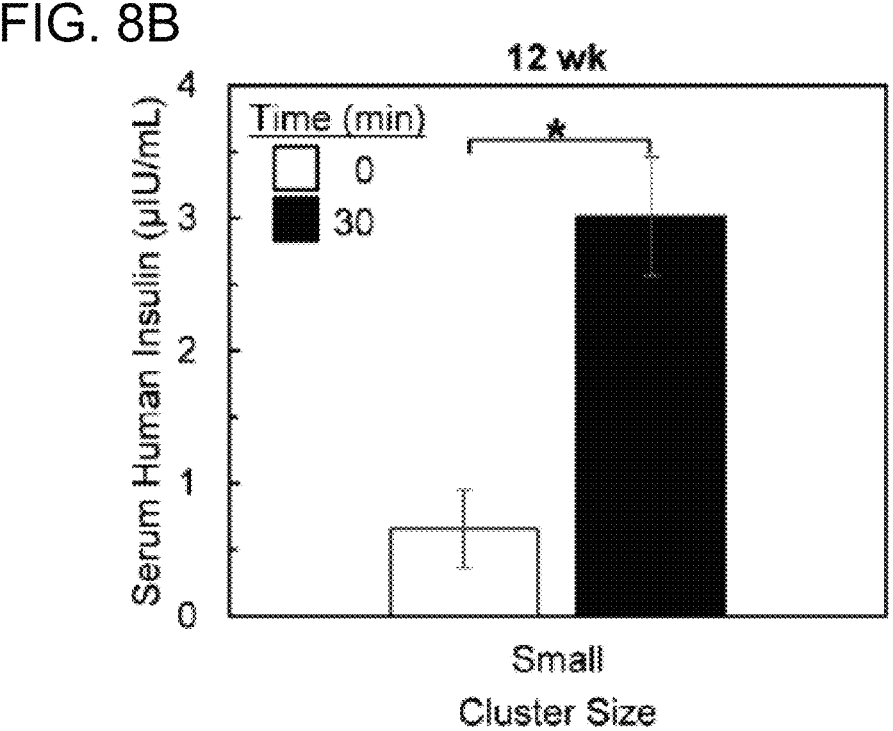
FIG. 8B shows n in vivo glucose stimulated insulin secretion assay of mice 12 weeks (n=3 for small clusters) after transplantation.
Figure 8C:
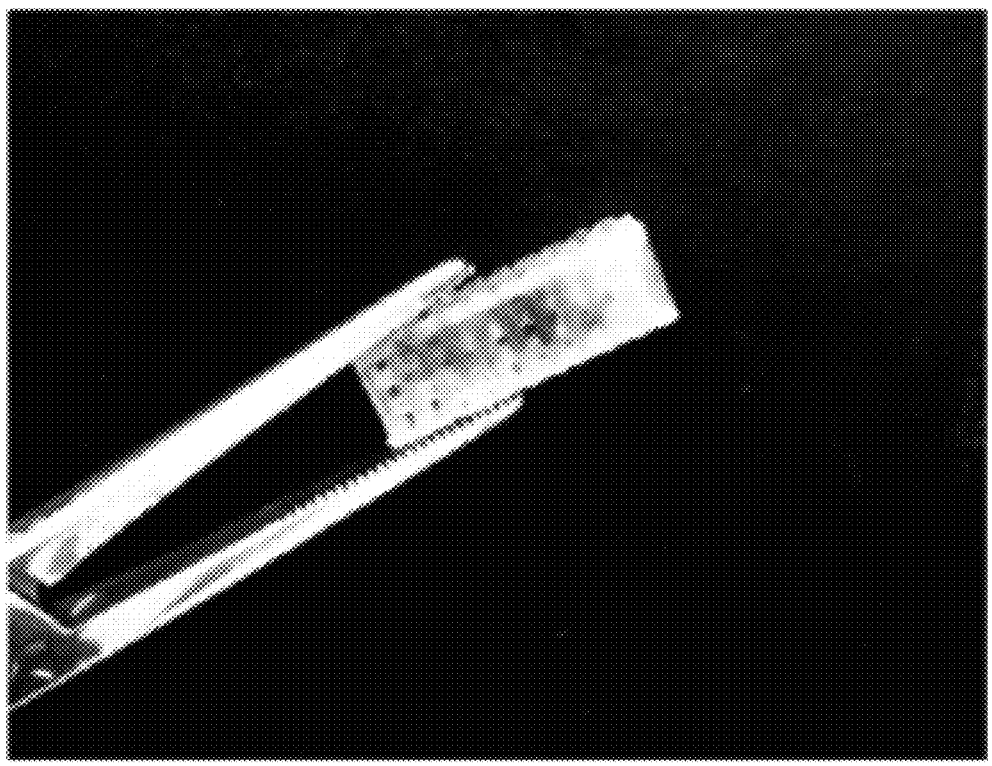
FIG. 8C is an image demonstrating handling of a recovered 3D-printed device.
Figure 8D:
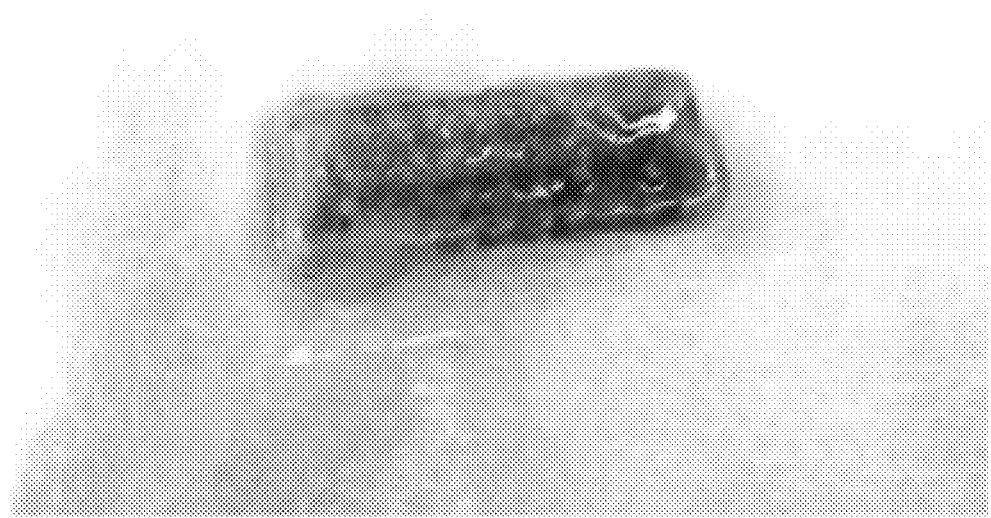
FIG. 8D is an image of a recovered 3D-printed device.
Figure 8E:
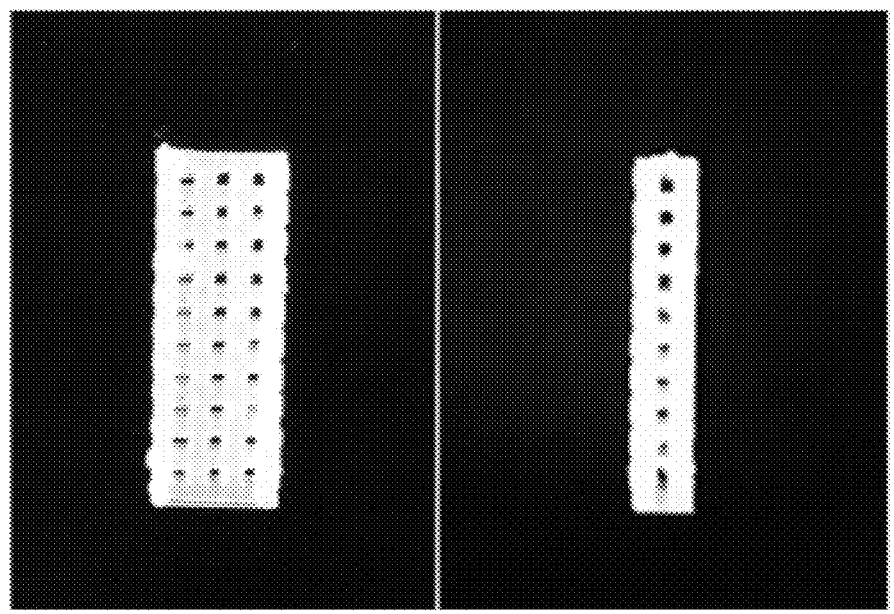
FIG. 8E is an image showing a decellularized recovered 3D printed device.
Figure 8F:
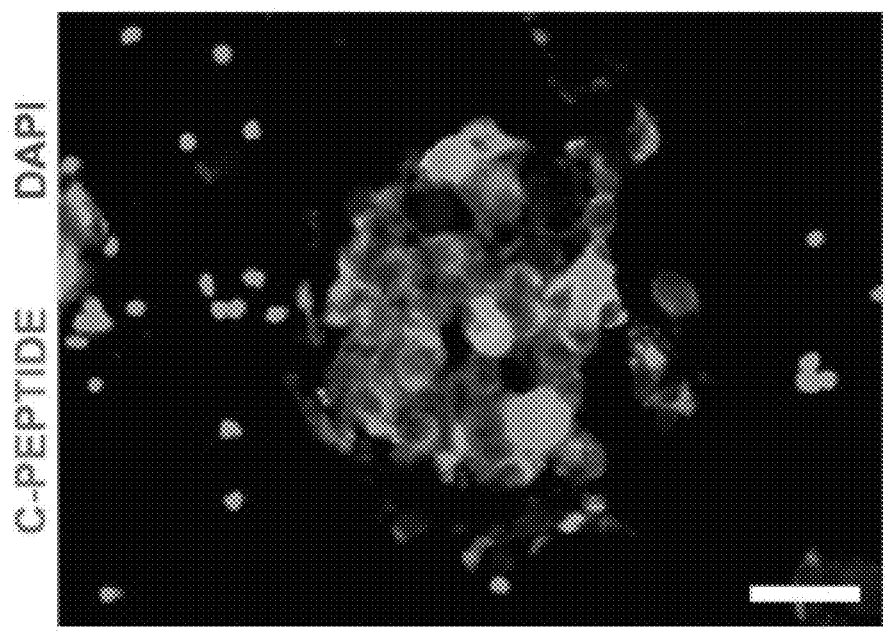
FIG. 8F is a histological section of tissue recovered from device stained for C-peptide (green) and with 4,6-diamidino-2-phenylindole (DAPI; blue). There are some red blood cells that autofluoresce green around the cellular cluster. Scale bar=25 μm. *p<0.01 (two-sided unpaired t-test when comparing large vs. smaller clusters, two-sided paired t-test when comparing 0 vs. 30 min).

The 3D-printing approach was validated by transplanting SC-β cell-loaded 3D-printed device subcutaneously into immunocompromised mice. FIG. 8 shows 3D-printed devices loaded with SC-β cells ($5 \times 10^6$ cells per mouse) are functional after transplantation into mice. Two groups of animals were compared that were transplanted with either large or resized small clusters. After 2 weeks in vivo, the functional status of the graft with a glucose-stimulated insulin secretion assay was evaluated. After fasting the mice overnight, serum was collected before and 30 minutes after an injection of glucose (FIG. 8A). Mice that received devices with large clusters had detectable human insulin in the serum but did not respond to the glucose injection, which is consistent with an unhealthy graft. Mice that received devices with small clusters also had detectable human insulin in the serum. In addition, the glucose injection caused a 2.5±0.4 times increase in human insulin, indicating that the transplanted grafts were functional and glucose-responsive. This in vivo functional phenotype was observed up to 12 weeks (FIG. 8B). After this 12 week observation period, the 3D-printed devices were still retrievable from the mice (FIG. 8C-8D). Devices maintained structural integrity and could be easily handled without risk of deformation. Some devices were placed in a decellularization solution to remove infilled mouse tissue and allow better visual inspection of the device (FIG. 8E). No visible defects were noted. Removal of cells for histological processing from the retrieved device without destroying the tissue was difficult, but it was observed that the presence of SC-β cell clusters in the few intact pieces of tissue that were managed to be removed (FIG. 8F). This demonstrates that the SC-β cell-embedded 3D-printed devices combined with cell cluster resizing to avoid hypoxia are functional when transplanted into mice and can be retrieved.

Example 20

Figures 9A, 9B:
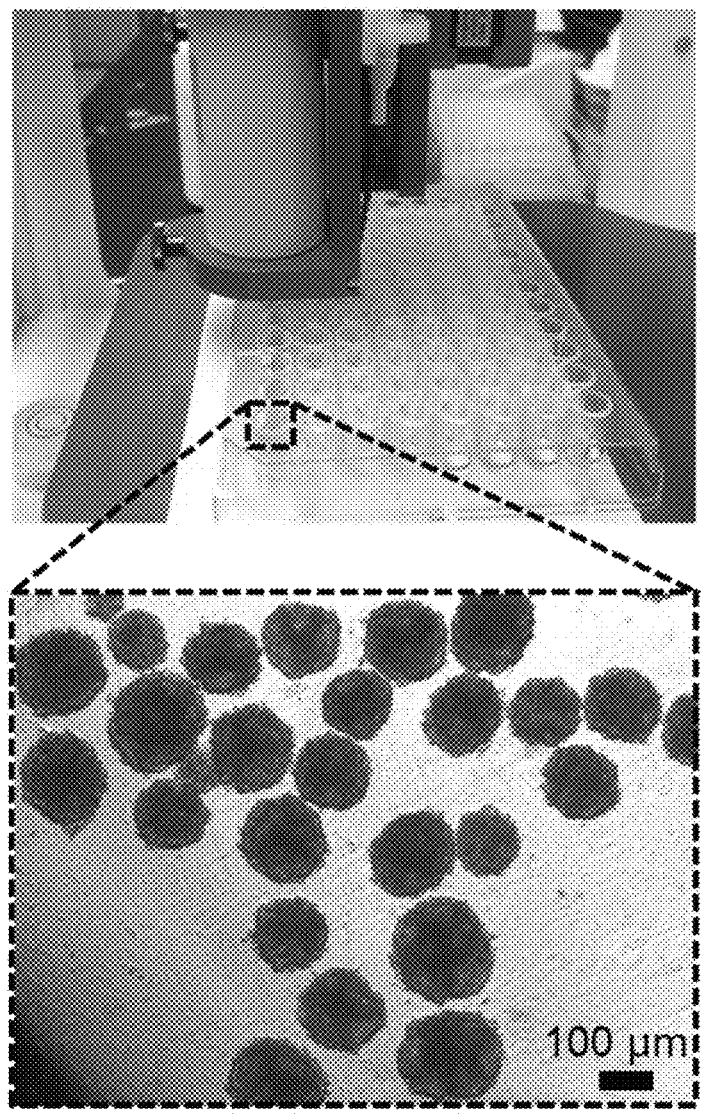
FIG. 9A is an image of a 3D bioprinter printing SC-β cell clusters into a 96-well plate.
FIG. 9B is a micrograph of SC-β cell clusters 3D bioprinted in gelatin methacrylate that has been cross-linked with UV light.
Figure 11A:
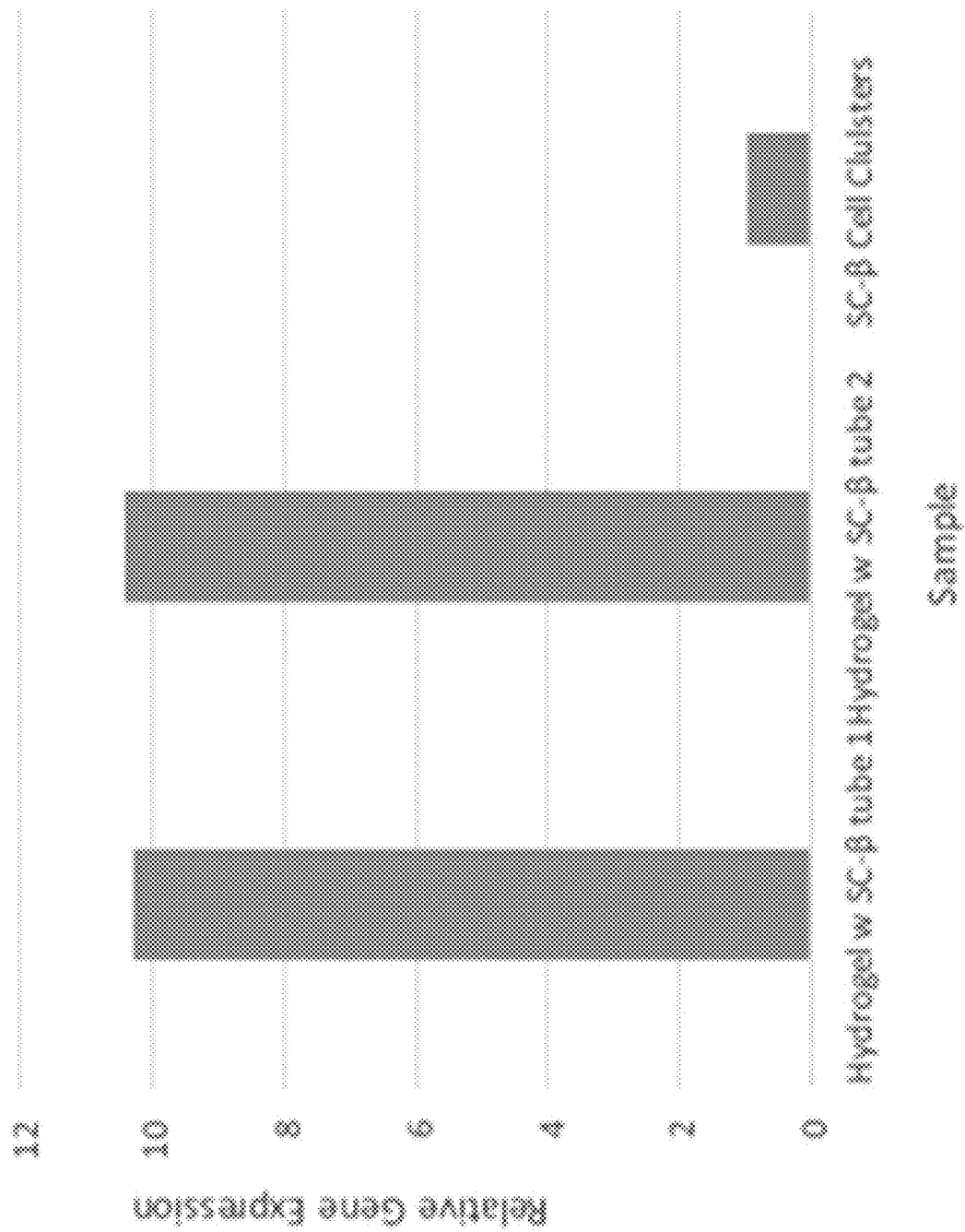
FIG. 11A is graph of gene expression of the beta cell gene PDX1 from real-time PCR for two 3D printed samples (hydrogel with SC-β tube 1 and hydrogel with SC-β tube 2) compared to SC-beta cells that were not 3D printed (SC-β Cell Clusters).
Figure 11B:
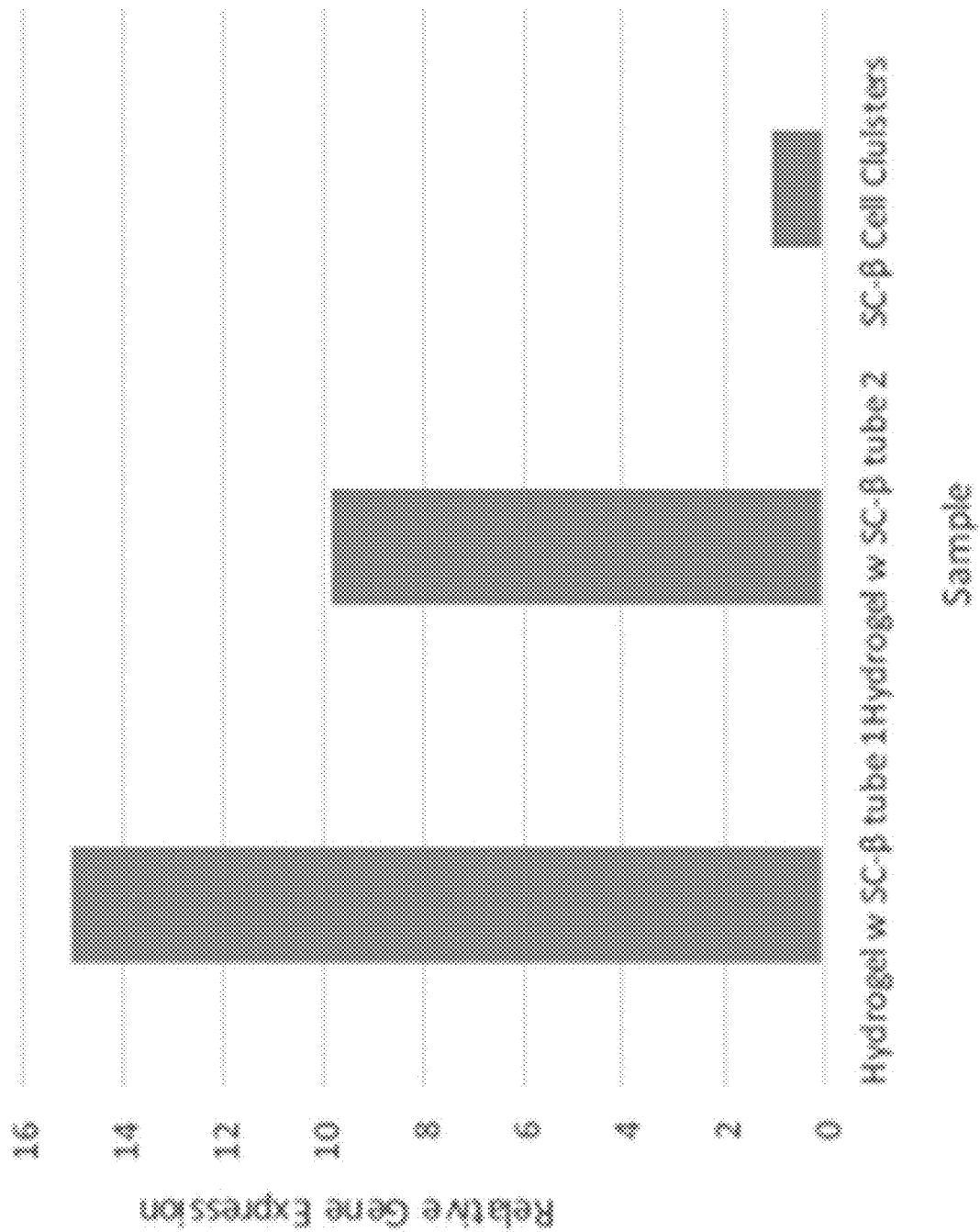
FIG. 11B is graph of gene expression of the beta cell gene INS (insulin) from real-time PCR for two 3D printed samples (hydrogel with SC-β tube 1 and hydrogel with SC-β tube 2) compared to SC-beta cells that were not 3D printed (SC-β Cell Clusters).

3D-Bioprinted SC-β Cells 3D bioprinting of SC-β cells to form the 3D printed device was validated by 3D bioprinting of SC-β cell clusters. CS-β cell clusters were first mixed with gelatin methacrylate. A 3D bioprinter (Biobot 1) was then used to print the SC-β cell clusters in the gelatin methacrylate into a 96-well plate (FIG. 9A). The gelatin methacrylate hydrogel can be photopolymerized with UV light to create the 3D-printed device with SC-β cells implanted in the device. FIG. 9B is a micrograph of SC-β cell clusters 3D bioprinted in gelatin methacrylate that has been cross-linked with UV light.

The 3D-printed SC-β cell clusters are viable after being printed. FIGS. 9A-9D show SC-β cell clusters stained with a LIVE/DEAD dye. The majority of cells are alive. Therefore, the CS-β cell clusters may be directly printed to create the device.

3D-printed SC-beta cells express beta cell markers. Real-time PCR was used to measure gene expression of the beta cell genes PDX1 and INS (insulin) for two 3D printed samples (hydrogel with SC-β tube 1 and hydrogel with SC-β tube 2) compared to SC-β cells that were not 3D printed (SC-β Cell Clusters). The results of the real-time PCR are in FIGS. 10A and 10B. SC-β cells were generated with a published method that produces cells that express these markers (Pagliuca et al. Cell 2014). 3D bioprinting maintained expression of these beta cell markers.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A 3D-printed device for transplanting cells into a patient, the device comprising:
   a 3D-printed biocompatible polymer scaffold comprising uniform pores; and
   a plurality of cells embedded in a degradable hydrogel, wherein a mixture of the plurality of cells and degradable hydrogel is housed within the pores of the 3D-printed biocompatible polymer scaffold,
   wherein the plurality of cells are stem cell derived β-cells.

2. The 3D-printed device of claim 1, wherein the plurality of cells in the device release a biologically active agent in response to a biological factor in the patient.

3. The 3D-printed device of claim 1, wherein the pores are less than 200 μm in length or diameter.

4. The 3D-printed device of claim 1, wherein the device has a length between about 10 mm and about 25 mm.

5. The 3D-printed device of claim 1, wherein the device has a width between about 5 mm and about 10 mm.

6. The 3D-printed device of claim 1, wherein the device has a thickness between about 2 mm and about 5 mm.

7. The 3D-printed device of claim 1, wherein the biocompatible polymer comprises polylactic acid (PLA), polycaprolactone, polyvinyl alcohol (PVA), gelatin methacrylate or combinations thereof.

8. The 3D-printed device of claim 1, wherein the degradable hydrogel comprises fibrin, collagen, alginate, triazole-thiomorpholine dioxide alginate, polyethylene glycol (PEG), PTFE, polyglycolic acid (PGA), poly-l-lactic acid (PLLA), polyhydroxyalkanoate, polycaprolactone-copolylactic acid, polylactide-coglycolide (PLGA), PDMS, polycaprolactone, gelatin methacrylate, or combinations thereof.

9. The 3D-printed device of claim 1, wherein the implanted cells are in a cluster, wherein each pore contains one cluster of cells.

10. A 3D-printed device for transplanting cells into a patient, the device comprising:
    a biocompatible polymer scaffold comprising uniform pores; and
    a plurality of cells housed within the pores of the biocompatible polymer scaffold,
    wherein the plurality of cells and biocompatible polymer are bioprinted to form the 3D-printed device, and wherein the plurality of cells are stem cell derived β-cells.

11. The device of claim 10, wherein the biocompatible polymer is gelatin methacrylate.

12. A method for transplanting cells into a patient comprising:
    embedding a plurality of stem cell derived β-cells into a degradable hydrogel;
    implanting the degradable hydrogel with the plurality of cells into pores of a 3D-printed device; and
    implanting the 3D-printed device into the patient.

13. The method of claim 12, wherein the plurality of cells are in a cluster, wherein each pore contains one cluster of cells.

14. A method of treating a patient in need thereof, comprising,
    implanting into the patient a 3D-printed device comprising a 3D-printed biocompatible polymer comprising uniform pores; a plurality of stem cell derived β-cells implanted within the pores of the 3D-printed biocompatible polymer; and a degradable hydrogel surrounding the plurality of cells,
    wherein the plurality of cells in the 3D-printed device release a biologically active agent in response to a biological factor in the patient.

15. The method of claim 14, wherein the biological factor is glucose.

16. The method of claim 14, wherein the biologically active agent is insulin.

* * * * *

SEQUENCE LISTING

```
<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: Homo Sapien

<400> SEQUENCE: 1
caatgccacg cttctgc                                                    17

<210> SEQ ID NO 2
```

```
<211> LENGTH: 20
<212> TYPE: DNA
<213> ORGANISM: Artificial Sequence
<220> FEATURE:
<223> OTHER INFORMATION: Homo Sapien

<400> SEQUENCE: 2
ttctacacac ccaagacccg                                               20

<210> SEQ ID NO 3
<211> LENGTH: 20
<212> TYPE: DNA
<213> ORGANISM: Artificial Sequence
<220> FEATURE:
<223> OTHER INFORMATION: Homo Sapien

<400> SEQUENCE: 3
ccgagtcctg cttcttcttg                                               20

<210> SEQ ID NO 4
<211> LENGTH: 20
<212> TYPE: DNA
<213> ORGANISM: Artificial Sequence
<220> FEATURE:
<223> OTHER INFORMATION: Homo Sapien

<400> SEQUENCE: 4
attcgttggg gatgacagag                                               20

<210> SEQ ID NO 5
<211> LENGTH: 18
<212> TYPE: DNA
<213> ORGANISM: Artificial Sequence
<220> FEATURE:
<223> OTHER INFORMATION: Homo Sapien

<400> SEQUENCE: 5
cgtccgcttg ttctcctc                                                 18

<210> SEQ ID NO 6
<211> LENGTH: 20
<212> TYPE: DNA
<213> ORGANISM: Artificial Sequence
<220> FEATURE:
<223> OTHER INFORMATION: Homo Sapien

<400> SEQUENCE: 6
cctttcccat ggatgaagtc                                               20

<210> SEQ ID NO 7
<211> LENGTH: 20
<212> TYPE: DNA
<213> ORGANISM: Artificial Sequence
<220> FEATURE:
<223> OTHER INFORMATION: Homo Sapien

<400> SEQUENCE: 7
tgacctcaac gatgcatttc                                               20

<210> SEQ ID NO 8
<211> LENGTH: 20
<212> TYPE: DNA
<213> ORGANISM: Artificial Sequence
<220> FEATURE:
<223> OTHER INFORMATION: Homo Sapien

<400> SEQUENCE: 8
```

```
ctgtcctggc tcttctgctc                                                    20

<210> SEQ ID NO 9
<211> LENGTH: 20
<212> TYPE: DNA
<213> ORGANISM: Artificial Sequence
<220> FEATURE:
<223> OTHER INFORMATION: Homo Sapien

<400> SEQUENCE: 9
gccataaggc atcattggac                                                    20

<210> SEQ ID NO 10
<211> LENGTH: 20
<212> TYPE: DNA
<213> ORGANISM: Artificial Sequence
<220> FEATURE:
<223> OTHER INFORMATION: Homo Sapien

<400> SEQUENCE: 10
aacaacagcc tgccacctta                                                    20
```